US007807454B2

(12) United States Patent
Oh et al.

(10) Patent No.: US 7,807,454 B2
(45) Date of Patent: Oct. 5, 2010

(54) MICROFLUIDIC MAGNETOPHORETIC DEVICE AND METHODS FOR USING THE SAME

(75) Inventors: Sang-Hyun Oh, Minneapolis, MN (US); Amarendra Kumar Singh, Jersey City, NJ (US); Yanting Zhang, Goleta, CA (US); Dharmakirthi Nawarathna, Tustin, CA (US); Unyoung Kim, Goleta, CA (US); Patrick Sean Daugherty, Santa Barbara, CA (US); Hyongsok Soh, Santa Barbara, CA (US); Brian Scott Ferguson, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 971 days.

(21) Appl. No.: 11/583,989

(22) Filed: Oct. 18, 2006

(65) Prior Publication Data

US 2008/0124779 A1 May 29, 2008

(51) Int. Cl.
*G01N 33/553* (2006.01)

(52) U.S. Cl. ..................... 435/308.1; 435/4; 435/173.9; 422/50; 422/51; 422/68.1; 422/82.05; 204/547; 204/643; 436/501

(58) Field of Classification Search ................. 204/547, 204/643; 422/50, 51, 68.1, 82.05, 186; 435/4, 435/308.1; 436/501, 518, 526, 514
See application file for complete search history.

(56) References Cited

U.S. PATENT DOCUMENTS 6,007,690 A 12/1999 Nelson et al.
6,010,607 A 1/2000 Ramsey
6,432,630 B1 * 8/2002 Blankenstein .............. 422/68.1
6,727,451 B1 4/2004 Fuhr et al.
6,736,978 B1 5/2004 Porter et al.
7,402,131 B2 * 7/2008 Mueth et al. .................. 494/36
2002/0036141 A1 * 3/2002 Gascoyne et al. ........... 204/547
2002/0166760 A1 11/2002 Prentiss et al.
2003/0044832 A1 3/2003 Blankenstein (Continued)

FOREIGN PATENT DOCUMENTS

DE 102004040785 A1 3/2006

(Continued)

OTHER PUBLICATIONS

Radisic et al, Micro- and nanotechnology in cell separation. Int. J. Nanomedicine 2006;1:3-14.
Hu et al. Marker-specific sorting of rare cells using dielectrophresis. PNAS, 2005, vol. 102, No. 44, pp. 15757-15761.
Herr et al. Integrated Microfluidic Platform for Oral Diagnostics. Annals of the New York Academy of Sciences, 2007, 1098, pp. 362-374.

(Continued)

*Primary Examiner*—Jill Warden
*Assistant Examiner*—Sharon Pregler
(74) *Attorney, Agent, or Firm*—Michael B. Rubin; Bozicevic, Field & Francis, LLP

(57) ABSTRACT

A microfluidic device may employ one or more sorting stations for separating target species from other species in a sample. The separation is driven by magnetophoresis. A sorting station generally includes separate buffer and sample streams. A magnetic field gradient applied to the sorting station deflects the flow path of magnetic particles (which selectively label the target species) from a sample stream into a buffer stream. The buffer stream leaving the sorting station is used to detect or further process purified target species labeled with the magnetic particles.

27 Claims, 20 Drawing Sheets

U.S. PATENT DOCUMENTS

| | | | | |
|---|---|---|---|---|
| 2003/0159999 | A1 | 8/2003 | Oakey et al. | |
| 2003/0175980 | A1 | 9/2003 | Hayenga et al. | |
| 2004/0018611 | A1 | 1/2004 | Ward et al. | |
| 2004/0166577 | A1 | 8/2004 | Storek et al. | |
| 2005/0079591 | A1 | 4/2005 | Reich et al. | |
| 2005/0121604 | A1 | 6/2005 | Mueth et al. | |
| 2005/0221604 | A1 | 10/2005 | He et al. | |
| 2005/0266394 | A1 | 12/2005 | Hatton et al. | |
| 2005/0266433 | A1 | 12/2005 | Kapur et al. | |
| 2005/0274650 | A1 | 12/2005 | Frazier et al. | |
| 2006/0020371 | A1 | 1/2006 | Ham et al. | |
| 2006/0177815 | A1 | 8/2006 | Soh et al. | |
| 2009/0047297 | A1 * | 2/2009 | Kim et al. ................ | 424/184.1 |

FOREIGN PATENT DOCUMENTS

| | | | |
|---|---|---|---|
| WO | WO9810267 | A1 | 3/1998 |
| WO | WO9949319 | A1 | 9/1999 |
| WO | WO0196857 | A2 | 12/2001 |
| WO | WO03046507 | | 6/2003 |
| WO | WO03046507 | A2 | 6/2003 |
| WO | WO03066191 | A1 | 8/2003 |
| WO | 2006/021410 | A1 | 3/2006 |
| WO | WO2007044642 | | 4/2007 |
| WO | WO2007092713 | | 8/2007 |

OTHER PUBLICATIONS

Mauk et al. Lab-on-a-Chip Technologies for Oral-Based Cancer Screening and Diagnostics. Annals of the New York Academy of Sciences, 2007, 1098, pp. 467-475.

Inglis. Continuous Microfluidic Immunomagnetic cell separation. Appl. Phys. Lett., 2004, vol. 85, No. 21, pp. 5093-5095.

Pamme, N., et al. On-chip free-flow magnetophoresis: Continuous flow separation of magnetic particles and agglomerates. Analytical Chemistry. 2004, vol. 76, pp. 7250-7256.

Certified Copy of priority document U.S. Appl. No. 60/764,390, filed Feb. 2, 2006 entitled "Microfluidic System and Method for Analysis of Gene Expression in Cell-Containing Samples and Detection of Disease."

Bessette, et al., Rapid isolation of high-affinity protein binding peptides using bacterial display., Protein Engineering Design and Selection 2004 17(10):731-739.

Miltenyi, et al., High gradient magnetic cell separation with MACS., vol. 11 Issue 2, pp. 231-238, Mar. 8, 2005.

Xia, et al., Combined Microfluidic-Micromagnetic Separation of Living Cells in Continuous Flow, Vascular Biology Program, Department of Pathology & Surgery, Children's Hospital and Harvard Medical School, Boston, MA, U.S. Appl. No. 60/724,117.

* cited by examiner

```
----WVMSFQDYKDLLKTH------(SED ID NO:01)
-----SQWVQDYKLLDPTRS-----(SED ID NO:02)
----EDGWGFDYKTLDVKL------(SED ID NO:03)
-RGLRSMFKSDYKDYD---------(SED ID NO:04)
---------SDYKRKDRWLSHESR-(SED ID NO:05)
------SKLKDYKMEDMRDNW----(SED ID NO:06)
------SHMTDYKCKDMRGGS----(SED ID NO:07)
---ANTTGSTDYKIHDPS-------(SED ID NO:08)
```

MICROFLUIDIC MAGNETOPHORETIC DEVICE AND METHODS FOR USING THE SAME

BACKGROUND

Sorting cells based on their surface markers is an important capability in biology and medicine. Magnetic Activated Cell Sorting (MACS) has become widely used as a cell sorting technique because it allows the rapid selection of a large number of target cells. The applications of MACS span a broad spectrum, ranging from protein purification to cell based therapies. Typically, target cells are labeled through a superparamagnetic particle that is conjugated to a molecular recognition element (e.g. a monoclonal antibody) which recognizes a particular cell surface marker.

Application of MACS has typically been limited to pre-enrichment before fluorescence-based cytometry. Nevertheless, due to its high throughput compared to other methods such as Fluorescence Activated Cell Sorting (FACS), MACS is still a widely used technology.

Current MACS systems are capable of high-purity selection of the labeled cells. However, they operate in a "batch mode" where the non-target and target cells are sequentially eluted after the application of the external magnetic field. In other words, the cells attached to magnetic particles are held in place while the unattached cells are eluted. Then, after this first elution step is completed, the magnetic field that prevented the magnetic particles from being eluted is removed and the magnetic particles can be eluted and recovered to recover target cells.

In order to achieve higher throughput and higher recovery of the rare cells (or other target components), improvements on existing MACS systems are needed.

SUMMARY

Embodiments of the invention provide a microfluidic device employing one or more sorting stations for separating target species from other species in a sample. The separation is driven by magnetophoresis. A sorting station generally includes separate buffer and sample streams. A magnetic field gradient applied to the sorting station deflects the flow path of magnetic particles (which selectively label the target species) from a sample stream into a buffer stream. The buffer stream leaving the sorting station is used to detect or further process purified target species labeled with the magnetic particles.

One aspect of the invention pertains to microfluidic sorting devices having the following features: (a) at least one inlet channel configured to provide separate streams of a sample and a buffer; (b) a sorting station fluidly coupled to the at least one inlet and located in a path of the sample stream; (c) a magnetic field gradient generator; and (d) at least one outlet channel configured to separately receive the buffer stream with deflected magnetic particles and a waste stream containing the sample at least partially depleted of the target species. The sample may include at least magnetic and non-magnetic particles. In some cases it includes a target species, non target species, and magnetic particles having an affinity for the target species in the sample. The buffer is generally substantially free of the sample. The magnetic field gradient generator is designed or configured to interact with an external magnetic field to produce a change in magnetic field gradient in the sorting station and thereby deflect the magnetic particles toward the buffer stream The sorting devices may have various flow inlet and outlet configurations. For example, the at least one inlet channel may include a first inlet channel for providing at least a portion of the buffer stream and a second inlet channel for providing at least a portion of the sample stream. In certain embodiments, the device may have (i) a first inlet channel for providing the buffer stream, and (ii) a second and third inlet channels for providing separate streams of the sample. The second and third inlet channels may be located on opposite sides of the first inlet channel, such that, during operation, the buffer stream enters a sorting station straddled by two sample streams. In certain embodiments, the reverse is true: the sample stream enters a sorting chamber straddled by two buffer streams.

In some embodiments, the outlet of sorting device includes (i) a first outlet channel for collecting at least a portion of the buffer stream containing purified target species; and (ii) a second outlet channel for collecting at least a portion of the sample stream. The second outlet channel may be sized and positioned to collect a separate portion of the buffer stream. In certain embodiments, the device includes (i) a first outlet channel for collecting at least a portion of the buffer stream containing purified target species; and (ii) a second outlet channel and a third outlet channel for collecting separate streams of the sample. In other embodiments, the first outlet channel is for collecting sample and the second and third outlet channels are for collecting buffer. In either case, the second and third outlet channels may be located on opposite sides of the first outlet channel.

The magnetic field gradient generator may also have various configurations. In certain embodiments, it includes a plurality of ferromagnetic elements (e.g., strips or pins) patterned on the sorting device proximate sorting station. These shape the magnetic field from an external source to provide a desired magnetic field gradient. The external magnetic field may be provided by a permanent magnet or an electromagnet proximate the plurality of ferromagnetic elements. In certain embodiments, the magnetic field gradient generator comprises two permanent magnets located on opposite sides of the plurality of ferromagnetic elements. In some embodiments, the plurality of ferromagnetic elements is disposed within a fluid pathway of the sorting station to allow fluid contact between the ferromagnetic elements and the sample stream. In certain embodiments, the plurality of ferromagnetic elements comprises ferromagnetic strips arranged in an angled configuration where the first ends of two ferromagnetic strips in the angled configuration touch or are separated by a first distance and the second ends of the two ferromagnetic strips are separated by a second distance, the second distance being greater than the first distance.

The sorting device may include one, two, or more magnetic field gradient generators, each imposing a magnetic field gradient on flowing magnetic particles. In some designs, at least two magnetic field gradient generators are located in fluid paths for two separate sample streams, which may be provided on opposite sides of a fluid path for a buffer stream.

In some designs, the sorting device allows magnetic particles to continuously flow past the magnetic field gradient generator without being captured. In other designs, the magnetic field gradient generator is configured to temporarily capture the magnetic particles and then release the magnetic particles to the at least one outlet channel.

Another aspect of the invention pertains to methods of sorting magnetic species in a sample. In some of these methods the sample includes a target species and magnetic particles having an affinity for the target species. Such methods may be characterized by the following sequence: (a) providing the sample to at least a first inlet channel of a microfluidic sorting device; (b) providing a buffer stream to the microfluidic sorting device; (c) magnetizing a magnetic field gradient generator to divert at least some of the magnetic species from the sample to the buffer stream; and (d) collecting at least a portion of the buffer stream comprising purified magnetic species at a collection outlet channel. In some embodiments, the collected magnetic species includes target species associated with magnetic particles.

The magnetic field gradient generator and the flow channel configuration may have various configurations as mentioned above. For example, providing the sample may involve providing two sample streams on opposite sides of the buffer stream in the microfluidic sorting device. Also, magnetizing the magnetic field gradient generator may involve applying an external magnetic field from a permanent magnet or an electromagnet to the magnetic field gradient generator.

The methods may include additional operations such as, but not limited to, detecting the purified target species in the collected buffer stream, amplifying a component, e.g., nucleic acid, of the target species in the microfluidic sorting device, lysing cells in the microfluidic sorting device, and separating components of the sorted target species, e.g., separating genetic material from target viruses, in the microfluidic sorting device.

Other methods involve (a) flowing a sample into a microfluidic sorting device having a magnetic field gradient generator to thereby capture at least some the magnetic particles; (b) removing or reducing a magnetic field applied to the magnetic field generator to thereby release captured magnetic particles; and (c) collecting purified target species with at least some of the magnetic particles at a collection outlet channel. In this method, the sample includes a target species and magnetic particles having an affinity for the target species.

Yet another aspect of the invention pertains to intergrated microfluidic devices or systems. In some embodiments, an integrated microfluidic sorting device includes the following elements: (a) a magnetic field gradient generator for exerting a magnetic force on a sample to divert magnetic particles in the sample to a collection channel; (b) an amplification station for amplifying nucleic acid of a target species associated with the magnetic particles in the collection channel; and (c) a detection station for detecting amplified nucleic acid. The microfluidic sorting device may also include a cell lysis station, a labeling station for labeling target species with magnetic particles, etc.

In certain embodiments, an integrated microfluidic sorting device includes the following elements: (a) a labeling station for labeling target species in a sample with magnetic particles having an affinity for the target species; (b) a magnetic field gradient generator for exerting a magnetic force on the sample to divert magnetic particles in the sample to a collection channel; and (c) a detection station for detecting the target species. In some cases, the device may also include a second labeling station for labeling diverted target species with a fluorophore having an affinity for the target species or for the magnetic particles. In some cases, the device may include a sample reservoir disposed upstream from the magnetic field gradient generator.

In still other embodiments, an integrated microfluidic sorting device may include the following elements: (a) a magnetic field gradient generator for exerting a magnetic force on a sample to divert magnetic labeled target species, e.g., cells or viruses, in the sample to a collection channel; (b) a first detection station for detecting magnetic labeled target species, e.g., cells or viruses, diverted to the collection channel; (c) a component release station for releasing components from the magnetic labeled target species, e.g., cells or viruses; and (d) a second detection station for detecting released components of the magnetic labeled target species, e.g., cells or viruses. Such a device may also include a component manipulation station for modifying released components to facilitate their detection in the second detection station. As an example, the component manipulation station may include an amplification station for amplifying nucleic acid of the magnetic labeled target species, e.g., cells or viruses. The device may optionally include a labeling station for labeling target species, e.g., cells or viruses, in the sample with magnetic particles having an affinity for a target species on surfaces of target cells or viruses.

These and other features and advantages of the invention will be presented in further detail below with reference to the associate drawings.

DESCRIPTION OF CERTAIN EMBODIMENTS

Introduction

Figure 1A:
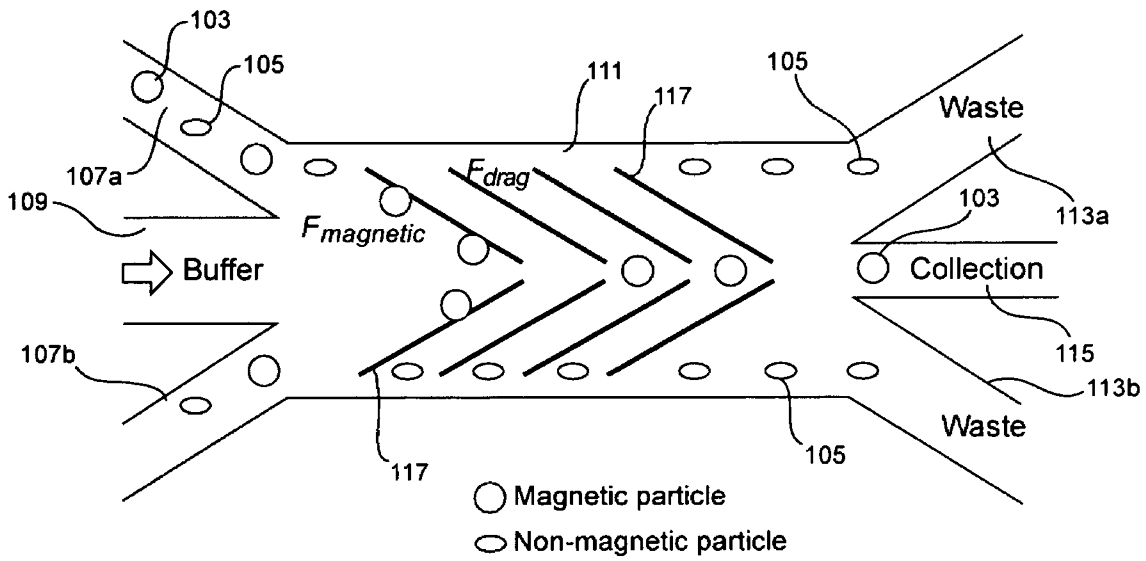
FIGS. 1A and 1B provide a top view of the channels and magnetic field gradient generating structures in one example of a microfluidics device.

In accordance with certain embodiments of this invention, a microfluidic device includes one or more magnetic field gradient generators (MFGs) useful for separating magnetic and non-magnetic particles in a continuous-flow system. The microfluidic devices of this invention may employ a laminar flow buffer switching configuration in which separate streams of buffer and sample are directed into separation regions of the microfluidic device. The combination of an MFG with a laminar-flow buffer switching scheme provides an efficient means for suppressing undesired mixing and rejecting non-target components so that the target components are purified with high efficiency. The device performance can be enhanced in some embodiments by providing integrated multiple MFG separation regions. These regions may be provided in series to improve enrichment and purity or in parallel to improve throughput. It is not uncommon to have five or more parallel multi-stage MFG separation stations on a single chip for applications requiring high throughput and purity.

The devices described herein enable sophisticated research applications such as high throughput library screening, patient care applications such as tumor cell and pathogen detection, as well as numerous industrial applications that involve separating magnetic materials (e.g., quality control applications). In some embodiments, magnetophoretic sorting stations allow fractionation of magnetic samples based on levels of magnetism in the sample. For example, target cells can be fractionated based the level of expression of a particular protein to which magnetic particles bind. Further, certain integrated devices and systems employ one or more "pre-processing" modules upstream of magnetophoretic sorting stations or "post-processing" modules downstream from the sorting stations. Examples of pre-processing modules include sample loading, filtering and tagging modules. Examples of post-processing modules include lysing, signal amplification, and detection modules.

While this document often uses the term "microfluidic," it should be understood that the principles and design features described herein can be scaled to larger devices and systems including devices and systems employing channels reaching the millimeter or even centimeter scale channels. Thus, when describing devices and systems as microfluidic, it is intended that the description apply equally to some larger scale devices. It should also be understood that when a channel or station is described herein it is understood that the described channel or station may be a single instance of multiple such channels or stations arranged to operate in parallel on a single substrate or on multiple substrates in an integrated system.

Note that the term microfluidic "device" is generally understood to mean a single entity in which multiple channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, that have microfluidic dimensions, e.g., as provided in greater detail below.

As an introduction, one example of a microfluidic device of this invention is depicted in FIG. 1. At various points herein, devices such as the one shown in FIG. 1 will be referred to as a "continuous-flow, magnetic activated cell sorters" (CMACS). As shown in the figure, a pattern of microfluidic channels is employed to separate magnetic particles 103 from non-magnetic particles 105. The microfluidic channels include sample inlet channels 107*a* and 107*b*, a buffer inlet channel 109, a sorting region 111, waste outlet channels 113*a* and 113*b*, and a collection channel 115. Within sorting region 111 multiple magnetic field gradient generators 117 are provided. These "magnetic field gradient generators" are elements that generate magnetic field gradients in a manner sufficient to alter the influence of an applied magnetic field on magnetically labeled species or intrinsically magnetic species in the sorting region by increasing or decreasing the field strength and/or changing the direction of the field. As explained more fully elsewhere herein, these magnetic field gradient generators serve to shape the distribution of the magnetic field gradient experienced by the particles traveling through the sorting region. In one embodiment, these are nickel strips provided within a flow channel of the sorting region itself. Not shown are one or more magnets that provide an external magnetic field in the sorting region. In one embodiment, a pair of permanent magnets such as NdFeB magnets is placed on the top and bottom of the sorting region. In other embodiments, one or more electromagnets may be employed to allow precise control of the field shape and homogeneity. The MFG strips interact with the field produced by the magnet to precisely shape and direct the magnetic field gradient within sorting region 111.

During operation, a buffer solution is introduced through buffer inlet channel 109 and a sample solution is introduced through sample inlet channels 107*a* and 107*b*. The sample solution may include magnetic particles and non-magnetic components from a sample being analyzed (e.g., whole cells, cell components, macromolecules, non-biological particles, etc.). The magnetic particles include a capture moiety that selectively binds with a target component in the sample. Typically, the buffer contains substantially no sample or analyte. However, in some embodiments, the buffer may include reagents for facilitating other operations (non-sorting operations) performed in an integrated microfluidics system (e.g., sample amplification or detection). The buffer and sample solution flow through the sorting region in the laminar regime. Effectively, they flow through the sorting region as uniaxial streams, with little or no mixing. The little mixing that does occur is primarily diffusion driven.

The magnetic and non-magnetic particles entering sorting region 111 through sample inlet channels 107*a* and 107*b* experience a strong magnetic field gradient imposed by the magnet and MFG strips 117. The gradient has no effect on non-magnetic materials, so the force on non-magnetic components 105 is primarily in the direction of the $F_{drag}$ arrow in FIG. 1. This is due to the uniaxial flow of the sample solution along the outer edges of sorting region 111. Magnetic particles 103, however, experience an effective force that is a vector sum of $F_{drag}$ and $F_{magnetic}$, which is the force exerted on them by the magnetic field gradient as they pass over MFG elements in the sorting region. As can be seen in the figure, the resulting force vector "guides" magnetic particles 103 along the magnetic strips and across a laminar stream boundary into the buffer stream (i.e., toward the center of sorting region 111). This process is sometimes referred to as "buffer switching." As a consequence of buffer switching, magnetic particles 103 are directed toward collection channel 115 in a buffer stream, while non-magnetic components 105 are directed toward waste outlet channels 113*a* and 113*b*. The output of collection channel 115 contains a significantly enriched composition of the target component, as carried by the magnetic particles. As indicated, the magnetic particles are typically coated with a target capture moiety.

Figure 1B:
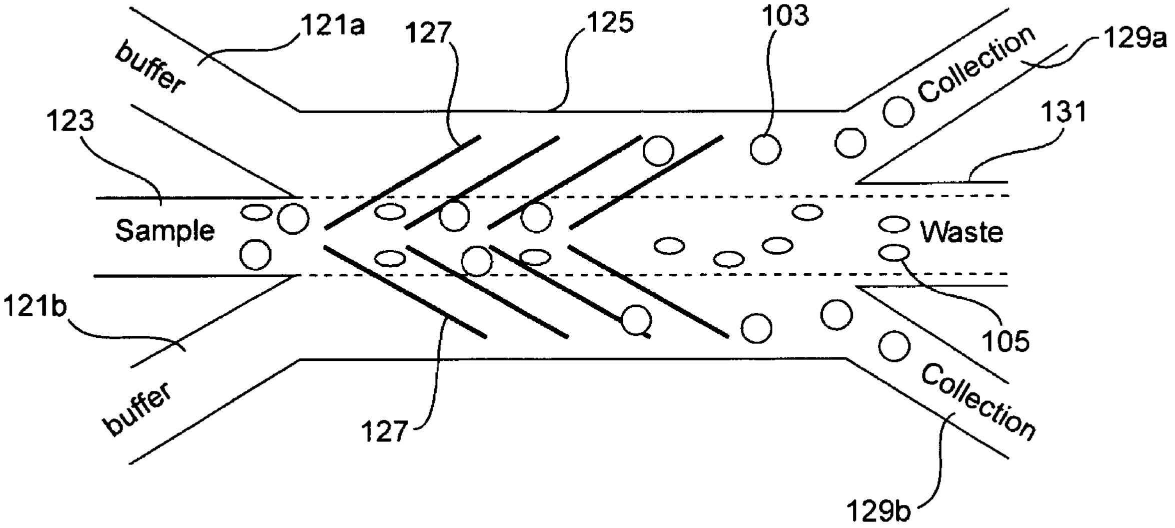

A different embodiment is shown in FIG. 1B. As shown in this figure, the locations of the sample and buffer streams are reversed such that sample (including magnetic particles 103 and non-magnetic particles 105) flows in a central stream of the sorting device and buffer flows in two outer streams straddling the sample stream. In this example, the MFGs again comprise a series of strips at the interfaces of the sample and buffer streams. However, the strips in this example are angled in the opposite direction (compared with the stripes in the embodiment of FIG. 1A) to thereby guide the magnetic particles out of the sample stream and into the peripheral buffer streams. In certain embodiments, the strips are configured so as to impart little if any influence on bulk fluid flow through the sorting region.

As shown in FIG. 1B, buffer enters the sorting station via inlet channels 121*a* and 121*b*. Sample enters via a central inlet channel 123 and flows as a stream along side the buffer streams in a sorting region 125. There, the sample stream encounters magnetic strips 127 which guide the magnetic particles 103 outward and into the buffer streams. The magnetic particles in the buffer streams exit collection channels 129*a* and 129*b*. Waste, including non-magnetic particles, exits a waste channel 131. This approach can provide an advantage of providing a sample stream that need not change direction upon entry into the sorting region. As a consequence, it is unlikely that cells or other analyte component will become attached the channel walls.

As can be seen from the relative dimensions of the inlet and outlet channels of the sorting stations of FIGS. 1A and 1B, some buffer streams "bleedout" and flows out the waste channel. This reduces the likelihood that components from the sample stream will pass through the collection channel. As a result, the high purity of target in the collection stream will not be compromised.

The relative dimensions of the channels together with the size and arrangement of the MFG structures are chosen to balance and optimize the desired throughput, purity, and recovery of the target from the sample stream. In addition, it is usually important to ensure that there will be no backflow in the channels. Some examples of MFG and hydrodynamic design parameters and appropriate value ranges for these parameters will be presented below.

Various computational tools are available for modeling the fluid flow and magnetic field gradients to ensure that the hydrodynamics and field gradient of a given design meet the necessary performance criteria. Examples of such tools include PSpice from Cadence Design Systems, San Jose, Calif., FemLab from Consol Ltd., Los Angeles, Calif., and Mathematica from Wolfram Research, Champaign, Ill.

In certain embodiments, the device performance is characterized in terms of one or more of the following metrics: throughput, purification, and recovery. Obviously, the actual values and balance of these performance metrics depend on the goals of the application and the unique set of technical constraints imposed by the application. Still it is worth considering these parameters for comparison to other devices. Example ranges that can be realized using embodiments of this invention will be presented below.

Magnetic Field Gradient Generating Structures

The magnetic field gradient is responsible for the magnetic force exerted on magnetic particles in microfluidic devices. In weakly diamagnetic media such as most buffer solutions, the magnetophoretic force on a paramagnetic particle can be approximated as $\vec{F}_{magnetic}=V_m\cdot\Delta\chi\cdot\nabla(B^2/2\mu_0)$, where ($\mu_0$) is the permeability of free space, B is the magnetic flux density, $\Delta\chi=\chi_{particle}-\chi_{medium}$ is the differential magnetic susceptibility of the particle relative to its suspension medium, and $V_m$, is volume of the paramagnetic particle. Thus, the force depends on the gradient of the square of the flux density B. For many applications such as those described below, where superparamagnetic particles are in the saturation regime, the total volume magnetization ($\vec{m}_p=V_m\cdot\Delta\chi\cdot\vec{H}$) is constant and the equation for the magnetophoretic force on a superparamagnetic particle can be simplified to $\vec{F}_{magnetic}=|\vec{m}_{sat}|\nabla(|\vec{B}|)$, where $m_{sat}$ is the saturated magnetization of the particle. Since the direction and magnitude of the force on a superparamagnetic particle are governed by the gradient of the applied field, magnetophoretic separation devices may be designed to accurately control this parameter.

The size and direction of the magnetic field gradient produced via an MFG depends on the applied magnetic field (typically provided by an external magnet proximate the sorting region) as well as the construction of the MFG. Pertinent parameters of MFG construction include the MFG material(s), the size and geometry of the MFG, and the orientation of the MFG with respect to the fluid flow and external magnetic field.

Of particular importance, the shape and arrangement or pattern of the elements making up an MFG should account for the hydrodynamics of the microfluidic device in the sorting channel. See for example the vector combination shown in FIG. 1. In certain embodiments, the direction of the gradient generated by an MFG be in a direction that promotes buffer switching toward a target collection region. In certain embodiments, the magnetic force exerted in this direction is greater than the component of drag force exerted in the opposite direction. Thus, in some embodiments, $F_d\cdot\sin\theta<F_m$, where θ is the angle between the direction of flow and the magnetic field gradient generating structures (for linear strips of these elements). An example of gradient magnitude and direction calculated with Mathematica™ is presented in the examples below.

The material from which an MFG element is made should have a permeability that is significantly different from that of the fluid medium in the device (e.g., the buffer). In certain cases, the MFG element will be made from a ferromagnetic material. Thus, the MFG element may include at least one of iron, cobalt, nickel samarium, dysprosium, gadolinium, or an alloy of other elements that together form a ferromagnetic material. The material may be a pure element (e.g., nickel or cobalt) or it may be a ferromagnetic alloy such as an alloy of copper, manganese and/or tin. Examples of suitable ferromagnetic alloys include Heusler alloys, (e.g., 65% copper, 25% manganese and 10% aluminium), Permalloy (55% iron and 45% nickel), Supermalloy (15.7% iron, 79% nickel, 5% molybdenum and 0.3% manganese) and μ-metal (77% nickel, 16% iron, 5% copper and 2% chromium). Nickel-cobalt alloys may also be used. In some embodiments, non-metallic ferromagnetic materials including ferrites which are mixture of iron and other metal oxides may be used. However, it may be challenging to fabricate MFGs from these materials for microfluidic devices.

Figure 2:
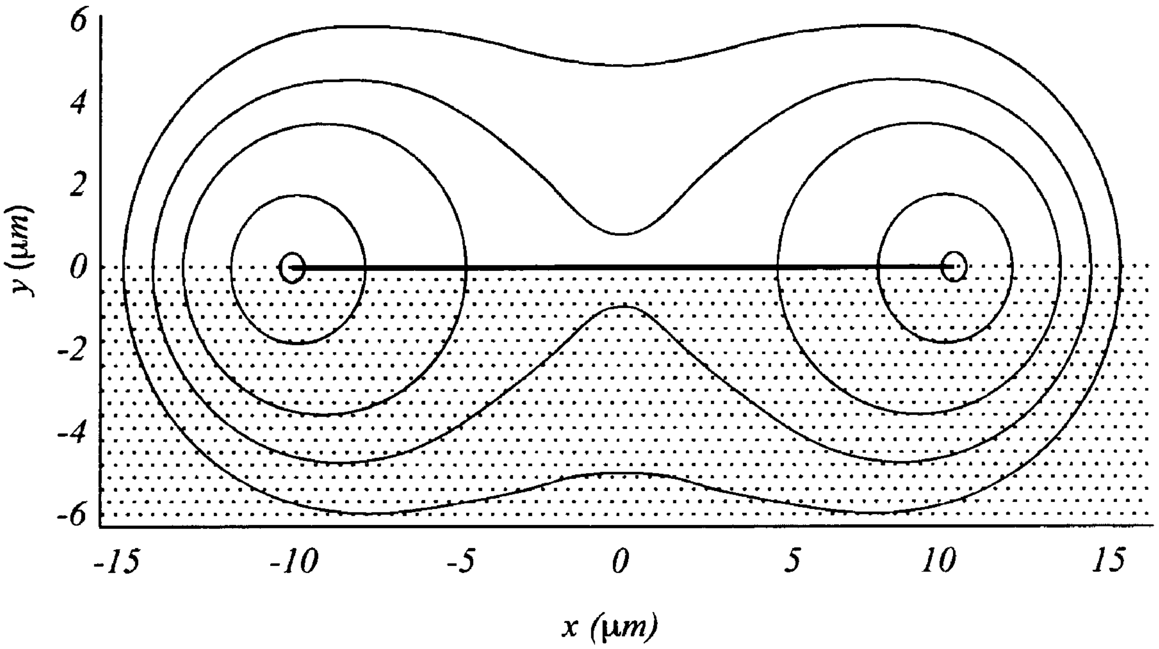
FIG. 2 is a cross sectional diagram of a magnetic field generating element showing contours of a simulated magnetic field distribution near the MFG element that is 20 μm in width and 0.2 μm in thickness, with the assumption that the external magnet magnetized the MFG element to saturation (6,000 Gauss) along the horizontal direction.

In the embodiment of FIG. 1, the MFG is an array of thin nickel stripes micro-patterned on a glass substrate, which becomes magnetized under the influence of an external permanent magnet. Because the nickel possesses much higher permeability than the surrounding material (i.e., the buffer), a strong gradient is created at the interface. Although the magnetic flux density from the MFGs may not be strong compared to the surface of the external magnet, the gradient of the magnetic field is very large within a short distance (e.g., a few microns in some embodiments) of the line edges (See FIG. 2). As a result, the MFGs allow precise shaping of the field distribution in a reproducible manner inside microfluidic channels. The MFG element may include one or more individual magnetizable elements. As shown in the FIG. 1, the MFG may include a plurality of magnetizable elements, e.g., 2 or more, 4 or more, 5 or more, 10 or more, 15 or more, 25 or more, etc.

In designs where the magnitude of the gradient decreases rapidly with distance from the MFG, the MFG may be formed within or very close to the flow channel where sorting takes place. Therefore, in some microfluidic examples, an MFG should be located within a few micrometers of the sorting region where magnetic particles are to be deflected (e.g., within about 100 micrometers (or in certain embodiments within about 50 micrometers or within about 5 micrometers of the sorting region, such as within about 2 micrometers of the sorting region). However, when large external fields are employed, the MFG design need not be so limited. Generally speaking, the MFG may be located as far away from the sorting region as about 10 millimeters. This may be the case when, for example, the external magnetic field is in the domain of about 1 Tesla or higher. Note that the large gradients afforded by such MFGs allow one to design very high throughput sorting stations with relatively large channels and consequently the capability to support large volumetric flow rates.

In certain embodiments, the MFG is provided within the sorting region channel; i.e., the fluid contacts the MFG structure. In certain embodiments, some or all of the MFG structure is embedded in channel walls (such as anywhere around the perimeter of the channel (e.g., top, bottom, left, or right for a rectangular channel)). Some embodiments permit MFGs to be formed on top of or beneath the microfluidic cover or substrate.

The pattern of material on or in the microfluidic substrate may take many different forms. In one embodiment it may take the form of a single strip or a collection of parallel strips. The example depicted in FIG. 1 shows four parallel strips comprising an MFG. Note that there are two MFGs in FIG. 1, one for the magnetic particles entering the sorting region from sample channel 107*a* and the other for magnetic particles entering the region from sample channel 107*b*.

Examples of suitable dimensions for line-type MFG structures will now be presented. In certain embodiments employing ferromagnetic strips for use in sorting particles in a conventional buffer medium, the strips may be formed to a thickness of between about 1000 Angstroms and 100 micrometers. The widths of such strips may be between about 1 micrometer and 1 millimeter; e.g., between about 5 and 500 micrometers. The length, which depends on the channel dimensions and the angle of the strips with respect flow direction, may be between about 1 micrometer and 5 centimeters; e.g., between about 5 micrometers and 1 centimeter. The spacing between individual strips in such design may be between about 1 micrometer and 5 centimeters. The number of separate strips in the MFG may be between about 1 and 100. The angle of the strips with respect to the direction of flow may be between about −90° and +90°. For fractionation applications, it has been found that angles of between about 2° and 85° work well. Obviously, one or more dimensions of the MFG pattern may deviate from these ranges as appropriate for particular applications and overall design features.

In certain embodiments, the pattern of ferromagnetic material may take the form of one or more pins or pegs in the flow channel or on the substrate beside the flow channel or embedded in the substrate adjacent the flow channel. FIGS. 3A to 3E present arrangements of ferromagnetic elements for MFGs in accordance with certain embodiments of the invention. In each case, the elements are provided within or proximate a flow channel in a magnetophoretic sorting region.

Figure 3A:
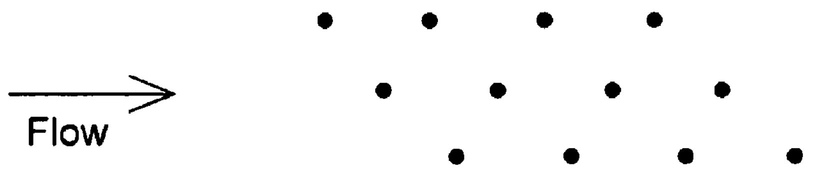
FIGS. 3A-3E are diagrams of various arrangements of peg or pin-type as well as strip and chevron-type magnetic field generating elements in accordance with various embodiments.
Figure 3B:
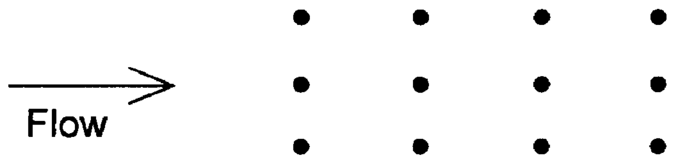
Figure 3C:
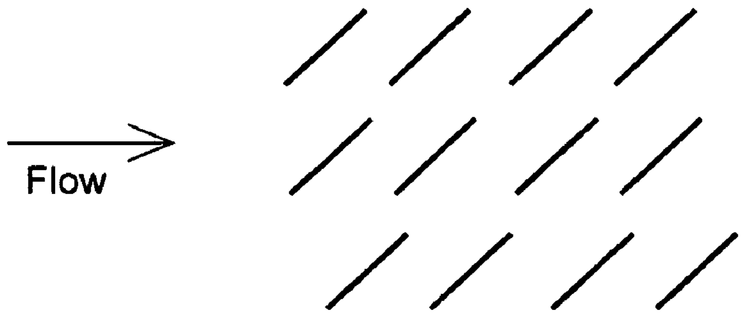
Figure 3D:
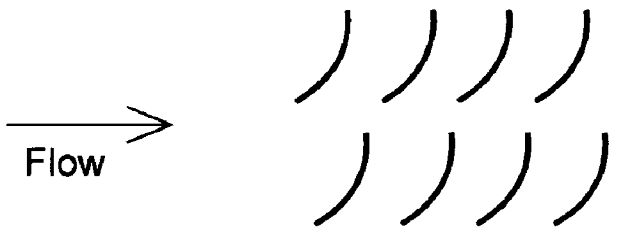
Figure 3E:
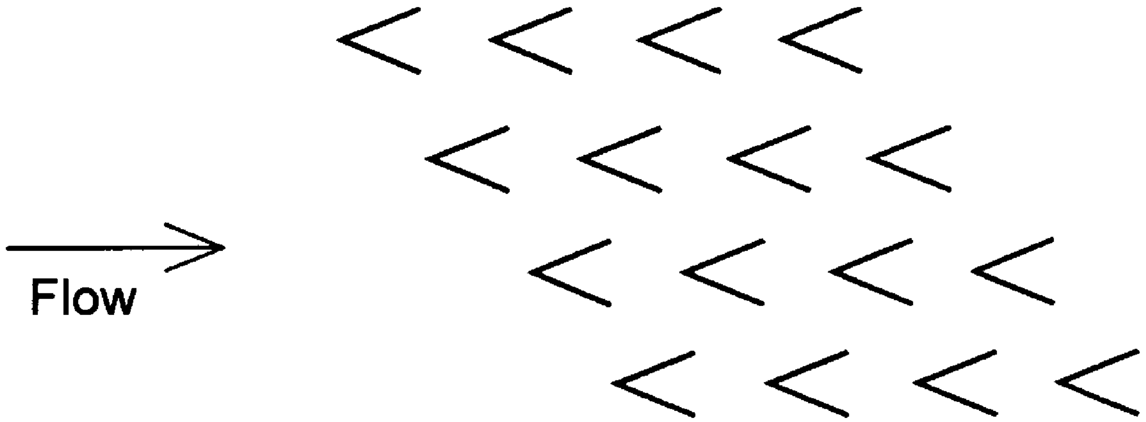

FIGS. 3A and 3B present two arrangements (rectangular and offset) of pin-type MFG elements depicted with respect to a direction of flow. The heights and widths of these elements may be in the same ranges as presented for the strip MFG elements presented herein. For comparison, FIGS. 3C-3E present arrangements of MFG elements taking forms of layers of linear strips (FIG. 3C), layers of curved strips (FIG. 3D), and layers of chevrons (FIG. 3E).

As indicated an external magnet may provide the magnetic field that is shaped by an MFG to produce a strong magnetic field gradient in a sorting region. Typically the external magnet is a permanent magnet, but it may also be an electromagnet (e.g., a Helmholtz coil). Generally, electromagnets produce smaller magnetic fields (in comparison to permanent magnets), but they may be designed to produce very uniform fields, which may be advantageous.

The position and orientation of the permanent magnet(s) with respect to the sorting region may be determined by the magnetic field strength produced by the permanent magnets, the homogeneity of the field (i.e., the uniformity of the field across the sorting region absent the MFG), the dimensions and shape of the magnet, etc. It generally desirable to have a uniform field produced by the external magnet(s) in the region of the MFG—assuming that the MFG is not present. In a typical case, two permanent magnets are employed, one located above the sorting region and the other located below the sorting region. In a specific embodiment, the magnets may be located above and below an MFG. In certain embodiments, two permanent magnets straddle a sorting region (i.e., the permanent magnets are located in the same plane as the sorting region or in a plane parallel to the plane of the sorting region). Certain embodiments employ a single magnet with one pole located above or below the sorting region. Still other embodiments employ generally U-shaped magnets in which poles at the terminal portions of the U straddle the sorting region (e.g., above and below or in the same plane).

In certain embodiments, the permanent magnet provides a field strength of between about 0.01 and 1 T, such as between about 0.1 and 0.5 T. Note that for some exotic applications, it may be appropriate to use stronger magnetic fields such as those produced using superconducting magnets, which may produce magnetic fields in the neighborhood of about 5 T.

Permanent magnets are made from ferromagnetic materials such as nickel, cobalt, iron, alloys of these and alloys of non-ferromagnetic materials that become ferromagnetic when combined as alloys, know as Heusler alloys (e.g., certain alloys of copper, tin, and manganese). Many suitable alloys for permanent magnets are well known and many are commercially available for construction of magnets for use with the present invention. A typical such material is a transition metal-metalloid alloy, made from about 80% transition metal (usually Fe, Co, or Ni) and a metalloid component (boron, carbon, silicon, phosphorus, or aluminum) that lowers the melting point. Permanent magnets may be crystalline or amorphous. One example of an amorphous alloy is $Fe_{80}B_{20}$ (Metglas 2605).

In a specific embodiment disclosed herein (an embodiment of the FIG. 1 design), the external magnetic field is provided by a pair of 5 millimeter diameter NdFeB magnets (K&J Magnetics, Jamison, Pa.) attached to the top and bottom sides of a sorting region in a microfluidic device.

In one specific embodiment that has been designed and built, the field gradient produced by the MFG was approximately 5000 T/m within 1 micrometer from the edge of the MFG. This device employed two 5 mm diameter external NdFeB magnets (K&J Magnetics, Jamison, Pa.) attached to the top and bottom sides of a sorting region. The MFG was provided as series of parallel strips, each having a thickness of about 0.2 micrometer, a width of about 20 micrometers. The individual strips were separated from one another by about 20 micrometers. Further, the angle of MFG strips was about 28° with respect to the flow direction.

The magnetic capture particles employed in microfluidic separations of this invention may take many different forms. In certain embodiments, they are superparamagnetic nanoparticles, although in some cases they may be ferromagnetic or paramagnetic.

As a general proposition, the magnetic particles should be chosen to have a size, mass, and susceptibility that allows them to be easily diverted from the direction of fluid flow when exposed to a magnetic field in microfluidic device (balancing hydrodynamic and magnetic effects). In certain embodiments, the particles do not retain magnetism when the field is removed. In a typical example, the magnetic particles comprise iron oxide ($Fe_2O_3$ and/or $Fe_3O_4$) with diameters ranging from about 10 nanometers to about 100 micrometers. However, embodiments are contemplated in which even larger magnetic particles are used. For example, it may be possible to use magnetic particles that are large enough to serve as a support medium for culturing cells.

Note that aggregation of magnetically labeled cells due to mutual magnetic interactions is generally undesirable, and may be avoided by using superparamagnetic nanoparticles. Thus, the magnetic particles may be commonly formed from single-domains of a ferromagnetic material (<100 nm iron oxide particles). In the absence of an external field, due to their small size, the thermal energy is sufficient to randomly orient their magnetization, resulting in a negligible average magnetization even below the Curie temperature. When an external field is applied, the magnetization of these superparamagnetic beads saturates at a relatively weak external magnetic field of ~0.02 T.

The magnetic particles may be coated with a material rendering them compatible with the microfluidics environment and allowing coupling to particular target components. Examples of coatings include polymer shells, glasses, ceramics, gels, etc. In certain embodiments, the coatings are themselves coated with a material that facilitates coupling or physical association with targets. For example, a polymer coating on a micromagnetic particle may be coated with an antibody, nucleic acid sequence, avidin, or biotin.

One class of magnetic particles is the nanoparticles such as those available from Miltenyi Biotec Corporation of Bergisch Gladbach, Germany. These are relatively small particles made from coated single-domain iron oxide particles, typically in the range of about 10 to 100 nanometers diameter. They are coupled to specific antibodies, nucleic acids, proteins, etc.

Another class of magnetic particles is made from magnetic nanoparticles embedded in a polymer matrix such as polystyrene. These are typically smooth and generally spherical having diameters of about 1 to 5 micrometers. Suitable beads are available from Invitrogen Corporation, Carlsbad, Calif. These beads are also coupled to specific antibodies, nucleic acids, proteins, etc.

It should be understood that certain embodiments make use of intrinsic magnetic properties of the sample material. In such embodiments, magnetic particles need not be employed. Examples of such materials include erythrocytes, small magnetic particles for industrial applications, etc.

Flow Systems and Hydrodynamics

Generally, the physical separation between the labeled and unlabeled sample components occurs through the balance between hydrodynamic and magnetophoretic forces. As the magnetically labeled components travel within the microfluidic channel, there exists a hydrodynamic drag force ($F_d$). Assuming that the magnetically labeled component is spherical, then the force can be approximated as $F_d = 6\pi\eta \cdot R_p \cdot \upsilon$, where $\eta$ is the viscosity of the medium, $R_p$ is the particle radius and $\upsilon$ is the velocity. When the labeled component passes over the MFGs at an angle as shown in FIG. 1, the MFG imposes an attractive magnetophoretic force ($F_m$). In this case, if the component of $F_d$ perpendicular to the MFG is less than the value of $F_m$ (i.e., $F_d \cdot \sin\theta < F_m$), then the velocity vector of the labeled cell will be significantly modified in the direction parallel to the MFG pattern, as demonstrated in FIG. 1.

In view of this, the linear fluid velocity in the sorting regions should be controlled to provide proper balance with the magnetic gradient size to ensure that efficient sorting can be accomplished. For a CMACS sorting region as depicted in FIG. 1, for example, a fluid velocity of approximately 3 mm/s has been found to be appropriate. At this velocity, viscous drag forces on Dynal M280™ 2.8 μm microbeads are expected to be ~160 pN (with $\eta$ ~0.002 $kg \cdot m^{-1} \cdot s^{-1}$ for the suspension medium). For a MFG oriented at approximately 28° with respect to the fluid direction and producing a field gradient of approximately 5000 T/m in the sorting region, a 3 mm/s allows efficient sorting. General ranges of fluid velocity suitable for use with various embodiments of the invention will be presented below.

Turning now to configurations of the sorting station, certain buffer switching designs will now be described. As explained, buffer switching employs separate streams of buffer and sample that are delivered to a sorting region. The force exerted on magnetic particles in the sorting region guides those particles out of the sample stream and into the buffer stream. Due to the low Reynolds number, the flow streams within the sorting region of a CMACS device are generally uniaxial and laminar (e.g., Re is approximately 2000 or less). Buffer switching regions may be designed such that in the absence of an external magnetic field, only the buffer medium arrives at a collection channel (see FIG. 1). When an external field is applied, the MFG elements become magnetized and the magnetically labeled components are selectively transported across the stream boundary, from the inlet stream into the buffer medium, resulting in a high purity of the target species in the collection channel. On the other hand, the unlabeled components (typically the majority of the components in the sample) are not deflected by the magnetic field and will enter the waste channels.

In buffer switching devices, the separate buffer and sample streams may be provided to the sorting region via one, two or more separate channels. Typically, though not necessarily, a sorting region will have at least one inlet channel dedicated to delivering buffer and another channel dedicated to delivering sample. In certain embodiments, at least one inlet channel to the separation region provides both the sample stream and the buffer stream. Because these streams are provided as laminar flows, they can be combined into an inlet channel upstream from the sorting region. They will then flow into the sorting region separated from one another as separate streams.

FIGS. 4A-4E present various buffer switching configurations. Each figure shows a distinct sorting region with at least one inlet channel and at least one outlet channel. Further each sorting region has at least one MFG, sometimes shown.

Figure 4A:
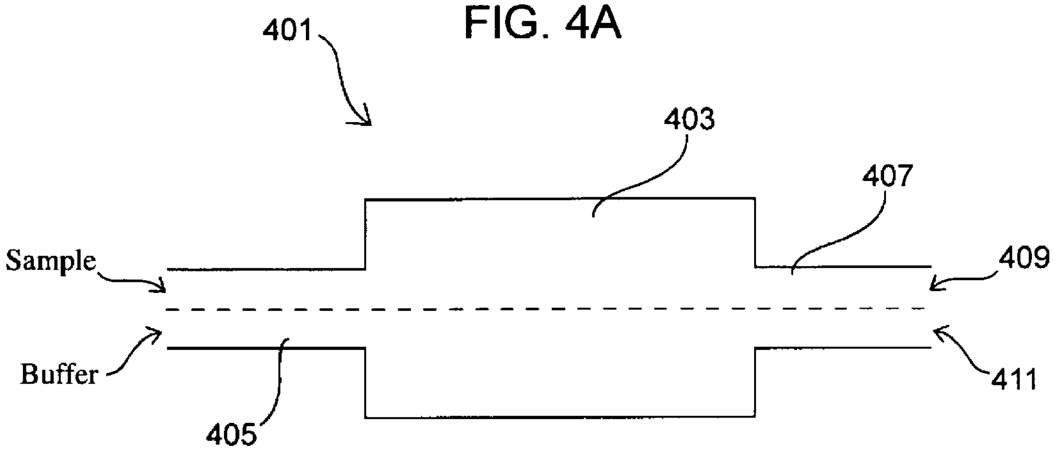
FIGS. 4A-4G are diagrams of various inlet and outlet channel configurations for buffer switching structures in accordance with certain embodiments.

FIG. 4A shows a simple configuration in which a buffer switching configuration 401 includes one inlet channel 405, one outlet channel 407 and a sorting region 403. The inlet channel 405 includes two laminar streams, a buffer stream shown in the lower portion of channel 405 and a sample stream shown in the lower portion of channel 405. The streams maintain their uniaxial flow trajectory through sorting region 403. At least one MFG (not shown) within region 403 imparts a "rightward" velocity component to magnetic particles entering through the sample stream in inlet channel 405. As a consequence, the magnetic particles are directed into the buffer stream and then exit through a buffer stream portion 411 of outlet channel 407. The non-magnetic components of the input sample remain in the sample stream and exit the sorting region 403 via a sample stream portion 409 of outlet channel 407.

Figure 4B:
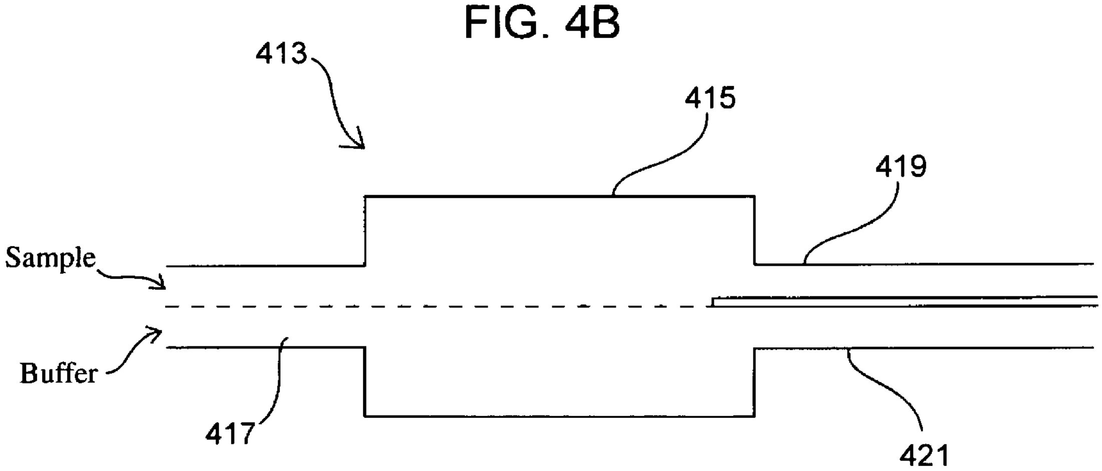

FIG. 4B shows a similar buffer switching configuration 413 but with two separate outlet channels: a dedicated waste or sample channel 419 and a dedicated buffer channel 421. In this embodiment, separate sample and buffer streams enter the lower and upper portions of an inlet channel 417. Together they flow into a sorting region 415 where at least one MFG (not shown) diverts any magnetic particles in the sample stream "rightward" into the buffer stream. The buffer stream, with diverted magnetic particles, exits the sorting region via a dedicated buffer exit channel 421. The sample stream, which has been depleted of magnetic particles, exists the sorting region via a dedicated waste exit channel 419.

Figure 4C:
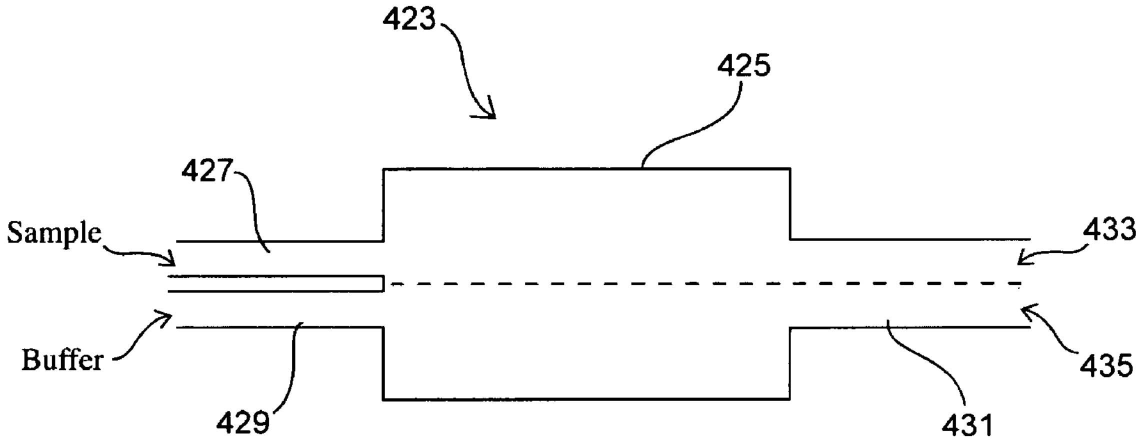

FIG. 4C shows another buffer switching configuration 423, this time with two inlet channels and a single outlet channel. In this embodiment, a sample stream is provided via a dedicated sample inlet channel 427. Similarly, a buffer stream is provided via a dedicated buffer inlet channel 429. The sample and buffer streams from the two inlets enter a sorting region 425 together, but remain as distinct uniaxial streams. Within the sorting region, at least one MFG imparts a downward velocity component to the magnetic particles in the sample stream. As a consequence, some or all magnetic particles in the sample stream cross the boundary between the sample and buffer streams and enter the buffer stream. The two streams exit the sorting region 425 together through an outlet channel 431. Within this channel a waste stream portion 433 carries the remainder of the sample stream, which has been depleted of magnetic particles. Also within outlet channel 431, a buffer stream portion 435 carries the buffer with the magnetic particles. As should be apparent, the contents of the outlet channels in the embodiments of FIGS. 4A and 4C must be separately treated downstream from the depicted sorting configurations. This may be accomplished, for example, via a downstream divide in the flow path or a chamber having separate treatment regions for the sample and buffer streams (e.g., a capture region for magnetic particles in the buffer stream).

Figure 4D:
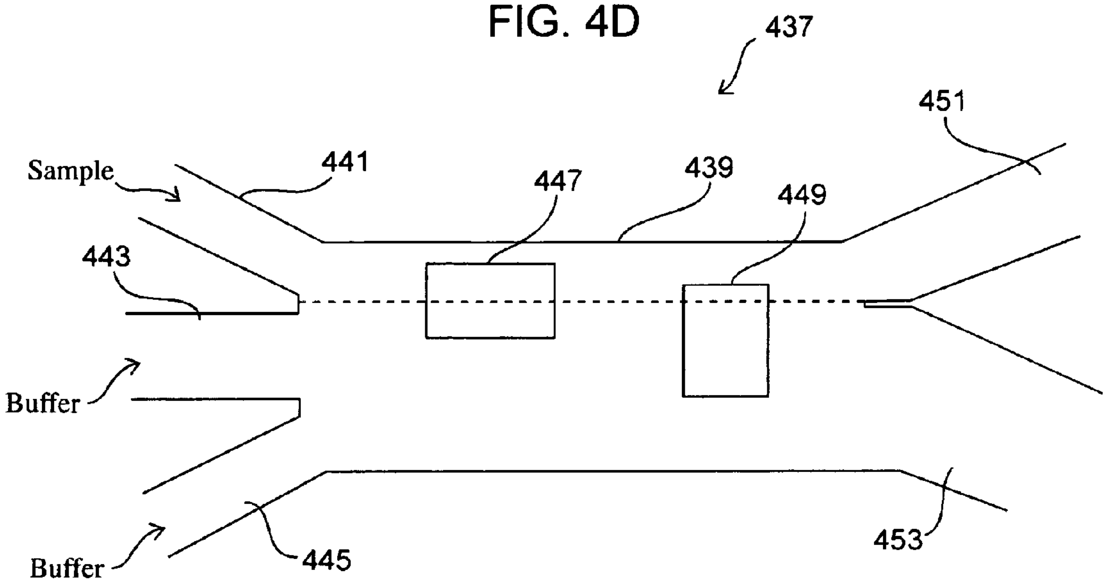

FIG. 4D shows a microfluidic sorting channel configuration 437 having three separate inlet channels and two outlet channels. Sample is provided via an inlet channel 441, while buffer is provided via two separate inlet channels 443 and 445 located below the sample inlet channel. Sample enters a sorting region 439 having two separate MFGs 447 and 449 arranged in series. Other MFG arrangements are possible in similar multi-channel sorting configurations. The MFGs in FIG. 4D divert magnetic particles from the sample stream (provided via inlet channel 441) toward and into the buffer stream(s) from inlet channels 443 and 445. The buffer stream(s) exit the sorting region via an outlet channel 453, while the sample stream (with a diminished or depleted concentration of magnetic particles) exits via a waste outlet channel 451. Note that the embodiment depicted in FIG. 4D allows for multiple buffer streams having potentially different compositions. In other embodiments, more buffer and/or sample inlet channels may be employed; e.g., three buffer inlet channels and two sample inlet channels may be employed. Further, in some embodiments, the number of sample inlet channels may be the same or greater than the number of buffer inlet channels; e.g., three buffer inlet channels and three sample inlet channels. Similar variations on the arrangement of outlet channels may be realized.

Figure 4E:
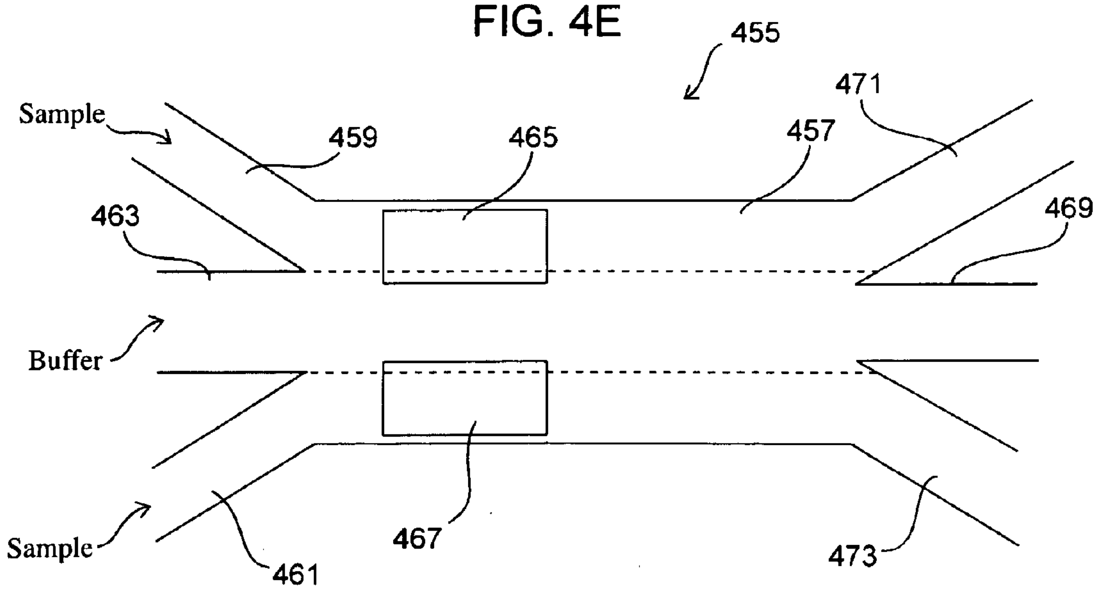

FIG. 4E depicts yet another arrangement 455 of channels for sorting. This embodiment provides a generic version of the sorting station depicted in FIG. 1. In the arrangement of FIG. 4E, two sample streams enter a sorting region 457 via inlet sample channels 459 and 461. These inlet channels straddle a buffer inlet channel 463. Thus, a buffer stream flows uniaxially through the sorting region along with sample streams on either side. In this embodiment, a first MFG 465 exerts a magnetophoretic force on magnetic particles entering from sample inlet channel 459, directing them downward into the central buffer stream provided via inlet 463. A second MFG 467 exerts a magnetophoretic force in the opposite direction, deflecting magnetic particles entering from sample inlet channel 461 upward into the central buffer stream. Thus, two parallel acting MFGs provide a high throughput concentrated target solution (sample components attached to the magnetic particles) through a buffer/target outlet channel 469. The depleted sample streams exit via waste outlet channels 471 and 473.

In some examples, the buffer and sample streams may be stacked vertically within a channel or sorting region. Obviously, devices such as those depicted in FIGS. 4A-4E, which are normally operated in horizontal arrangement can be turned by 90 degrees to a vertical orientation. However, a device may also be designed such that when the substrate lies flat on a surface, the buffer and sample streams flow within the sorting region on top of one another. One example of such device is depicted in FIG. 4F (cross sectional view) and 4G (top view).

Figure 4F:
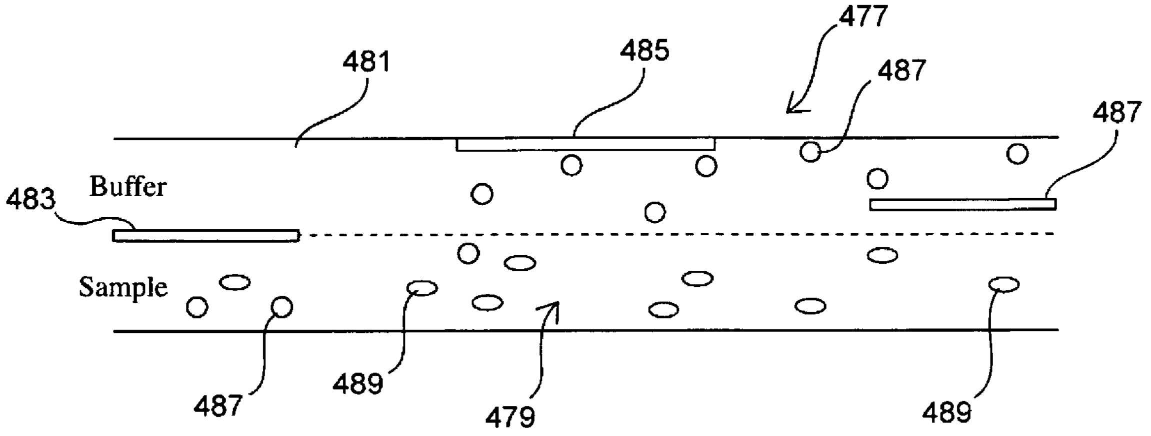
Figure 4G:
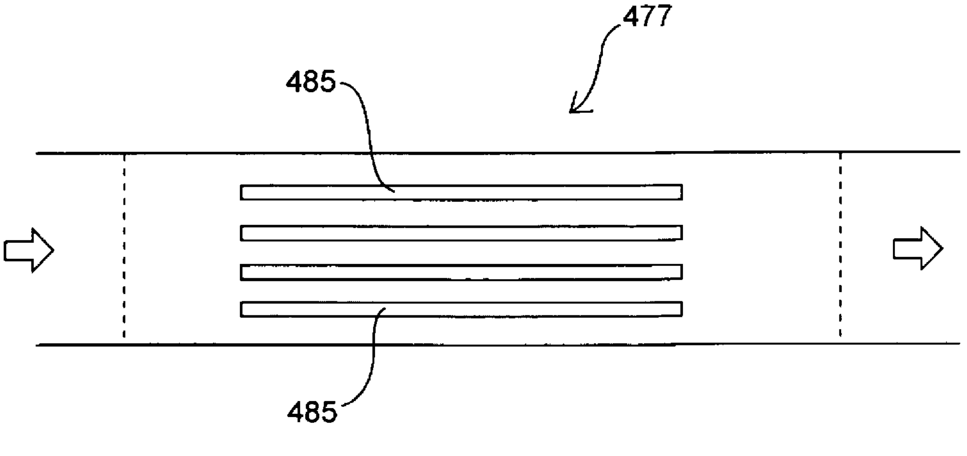

As shown in FIGS. 4F and 4G, a vertical sorting station 477 includes vertically stacked sample and buffer streams (479 and 481, respectively) flowing left to right, with the buffer stream flowing over top the sample stream in this example. Magnetic and no-magnetic particles (487 and 489, respectively) enter with the sample stream. A vertical separator 483 at the inlet side of station 477 defines the terminus of separate conduits for sample and buffer streams 479 and 481. Flowing past separator 483 the two streams are in contact and exposed to a magnetic field gradient produced using a series of parallel MFG strips 485 oriented in the direction of flow. As shown in FIG. 4F, magnetic particles are attracted toward the MFG strips and deflect upward into the buffer stream 481. They flow out of the sorting station in the buffer stream through a conduit defined by a separator 487. As shown in FIG. 4F, the interface between streams 479 and 481 is depicted as a dotted line. The relative positions of separators 483 and 487 allow bleedout of the buffer solution into the lower outlet—which is a waste channel.

Many other buffer switching structures are within the scope of the invention. In an example presented below, for instance, a multi-layer network or flow channels is provided with the buffer channels being provided at one layer of a device and the sample channels being provided at a different layer of the device. In this manner, the paths of the various flow lines can cross over one another without actually intersecting (analogous to multiple layers of metallization in an integrated circuit design). In some embodiments, the buffer and sample lines come together on the same level only as necessary to implement sorting modules. Such designs permit single entry ports for sample and buffer (as well as single outlet ports for waste and target collection) while providing parallel processing for high throughput.

The above embodiments contemplate that magnetic particles (e.g., magnetically labeled target species) move through the sorting station during a sorting a process. While this movement is typically envisioned to be continuous, that is not necessarily the case. In some cases, during their transport the magnetic species may become temporarily suspended against the flow of sample and/or buffer mediums. This situation becomes increasingly likely as the force exerted on the magnetic particles by the MFGs increases relative to the force exerted by the flow field.

In some embodiments, a sorting device is designed to temporarily hold magnetic particles in place within the sorting station. Later, they are released and collected. In such embodiments, the magnetic particles stop moving through the sorting station while the other sample components (non-magnetic) flow through and out of the station, thereby purifying the magnetic particles. Only after the non-magnetic sample components have flowed out of the sorting chamber are the magnetic components released and separately collected at an outlet of the sorting station. The design of the sorting station may be relatively simple such as the designs shown in FIGS. 1A, 1B, 4A, 4C, 4F, etc.

In a typical example, the sample flows into the sorting station, with or without concurrently buffer flowing. The MFG is controlled to provide a field gradient that is sufficiently strong to the hold most magnetic particles in place against the hydrodynamic drag force exerted by the flowing fluid. After most or all of the sample has flowed clear of the sorting station, the magnetic components may be released by modifying the magnetic field gradient and/or increasing the hydrodynamic force. Concurrently, buffer may be introduced into the sorting station so that the previously suspended magnetic components (now purified) flow out of the chamber in a buffer solution. In certain embodiments, the magnetic field of an MFG is controlled using an electromagnet so that a strong field gradient is produced early in the process (during capture of the magnetic particles) and then reduced or removed later in the process (during release of the particles). In other embodiments, permanent magnets may be used, which are mechanically movable into and out of proximity with the MFG elements (e.g., strips, pins, etc.), such that the magnetic field gradient in the sorting region can be increased and decreased to effect capture and release of the magnetic particles.

A capture and release protocol such as this is particularly advantageous when using relatively small target species such as viruses which have a tendency to become entrained in a boundary layer of a flow field within a microfluidic device. In certain embodiments, the following sequence of operations is employed. First, a sample such as a nasal swab potentially containing viral or components expressing a target moiety is mixed with small magnetic nanoparticles coated with a capture moiety (e.g., an antibody) specific for the target moiety. This mixing may take place on or off the microfluidic sorting device. After this labeling, the sample is then and flowed into a sorting station having an MFG which can have its magnetic field temporarily removed or reduced as described. If the sorting chamber has multiple inlets, buffer may be delivered through one or more of these inlets and sample through one or more others. After flowing a defined quantity of sample through the sorting chamber (e.g., all of the sample), the magnetic field to the MFG is reduced or removed and concurrently the sample inlet flow is replaced with buffer flow such that only buffer flows through the sorting station. The purified sample component presenting the target moiety is then collected at an outlet of the sorting chamber, which may be located directly downstream from MFG elements that held the magnetic particles.

Generally, the buffer entering the sorting region should contain little if any sample. It should provide a medium for collecting relatively pure target material from the sample, as carried by the magnetic particles. Therefore it preferably should contain relatively little sample material that might interfere with subsequent detection and/or treatment of the target material. Further, the buffer should be compatible with both the target and the magnetic particles that carry the target. Thus, the buffer may aqueous or non-aqueous depending on the sample being analyzed. For some applications, the buffer should have a density and composition that maintains magnetic particles and/or the sample materials in suspension. In certain embodiments, the density of buffer is between about 1 and 1.2 g/ml.

Some commonly used sorting buffers include phosphate buffered saline, deionized water, etc. Obviously, the actual buffer composition depends on the application and the nature of the sample and target. In a specific embodiment used to sort bacteria, the buffer comprises 1×PBS (phosphate buffered saline)/20% glycerol/1% BSA (bovine serum albumin) (all by volume) and has a density of 1.06 g/ml.

In certain embodiments, a sorting stage operates in constant flow processes to effect sorting. This does not mean that certain sorting operations cannot be performed without interruption of fluid flow. For example, in certain embodiments it may be necessary to intermittently pause the flow for process tuning or for certain designated operations such as detection, amplification, and/or lysis.

During constant flow conditions, the overall flow rate within the magnetophoretic sorting region of a microfluidic device will depend upon throughput goals as well as the total area of the channels and the resistance of the channels within the device. In certain embodiments, the process is performed with a volumetric sample flow rate of between about 10 μL/hour and 500 ml/hour. Typically, the high end of this range is attained with a multi-station parallel flow device or system. For a single sorting station, the sample flow rate may be between about 10 and 5000 μL/hour (preferably between about 50-1000 μL/hour), and the buffer flow rate of about 1-10 times that of the sample flow (preferably 2-4 times the sample flow). In a typical CMACS device, the fluid velocity in the sorting region is between about 100 μm/s and 50 cm/s, typically in the range of about 1-10 mm/s (e.g., approximately 2-5 mm/s).

Generally, sorting stages should be designed so that little if any unlabeled components cross the stream boundaries by diffusion. This may be accomplished by designing the device to have a relatively fast flow rate in the sorting region, and/or a relatively large distance for sample to traverse from a sample stream to a collection outlet channel. As an example, the typical diffusivity of a 1 μm-sized cell in an aqueous buffer at room temperature is D=0.2 $\mu m^2/s$. At a velocity of few mm/s, the dwelling time of each cell in the channel is typically less than a second, during which the cell can diffuse by only a few microns. If the device is operated such that a portion of the buffer stream is bled into the waste channel with a width >10 μm, which ensures that non-target cells that are able to cross the stream boundary through diffusion are unable to enter the collection channel.

Typical dimensions suitable for use with a single sorting region having at least one buffer inlet channel, at least one sample inlet channel, at least one outlet collection channel and at least one waste channel will now be presented. Depending on the relative amounts of target and non-target species, the ratio of cross sectional area of the collection channel(s) to cross sectional area of the waste outlet channel(s) may be about 100:1 to 1:100. Further, the ratio of cross sectional area of the buffer inlet channel to cross sectional area of the sample inlet channels may be about 100:1 to 1:100.

For further context, typical channel dimensions suitable for use with the microfluidic device of FIG. 1 will now be presented. In this example, all channels may have the same depth, e.g., approximately 1 micrometers to 10 millimeters depending on the magnetic field gradient size, although typically not greater than about 100 micrometers (e.g., 50 micrometers). In certain embodiments, the width of a waste outlet channel is in the range about 10 micrometers to 5 centimeters, although it is typically at least about 500 micrometers. The width of a collection channel may be between about 1 micrometer to about 5 centimeters (e.g., 80 micrometers). The width of a sample or buffer inlet channel may be approximately that of a waste outlet channel (e.g., about 10 micrometers to 5 centimeters, although typically at least about 500 micrometers). Additionally, the total width of the separation region may be, in certain embodiments, the sum of the widths of all inlet channels or all outlet channels.

The channels, inlets, vias, pumps, etc. required for a microfluidic sorting station of this invention may be fabricated using well know fabrication techniques (e.g., various microfabrication procedures) or purchased as necessary. In a specific example, borosilicate glass wafers may be affixed to PDMS replicas of a silicon master mold fabricated by applying a precursor to the silicon master, followed by curing. A binding agent such as epoxy may be used to bond the glass and PDMS layers.

Fluid flow may be either pressure-driven or electrokinetic-driven. Pressure-driven flows are created by pumps (e.g., peristaltic pumps), syringes, etc. that are readily available for small volume microfluidics applications. In a specific embodiment, a dual-track programmable syringe pump (Harvard Apparatus Ph.D. 2000, Holliston, Mass.) is employed to deliver both the sample mixture and the sorting buffer into the device at constant flow rates.

The flow of sample in the microchannel may be monitored through a suitable detector such as a bright-field microscope (e.g., the DM 4000, LEICA Microsystems AG, Wetzlar, Germany) and a cooled CCD camera (e.g., the ORCA-AG, Hamamatsu Corporation, Bridgewater, N.J.).

Multi-Stage Sorting

Two or more sorting stages may be integrated on a single microfluidic system or even a single microfluidics chip in a sequential manner to improve purity. Further, in certain embodiments, at least two sorting stations are provided in parallel to improve throughput. In certain embodiments, at least three sorting stations are provided in parallel, and in certain embodiments at least four sorting stations are provided in parallel. Likewise, in certain embodiments, at least two, three, or four sorting stations (or stages) are provided in series. Frequently, when multiple stages are provided in series at least two of the upstream stations are provided in parallel. Their outputs may combine to feed a downstream station.

Figure 5A:
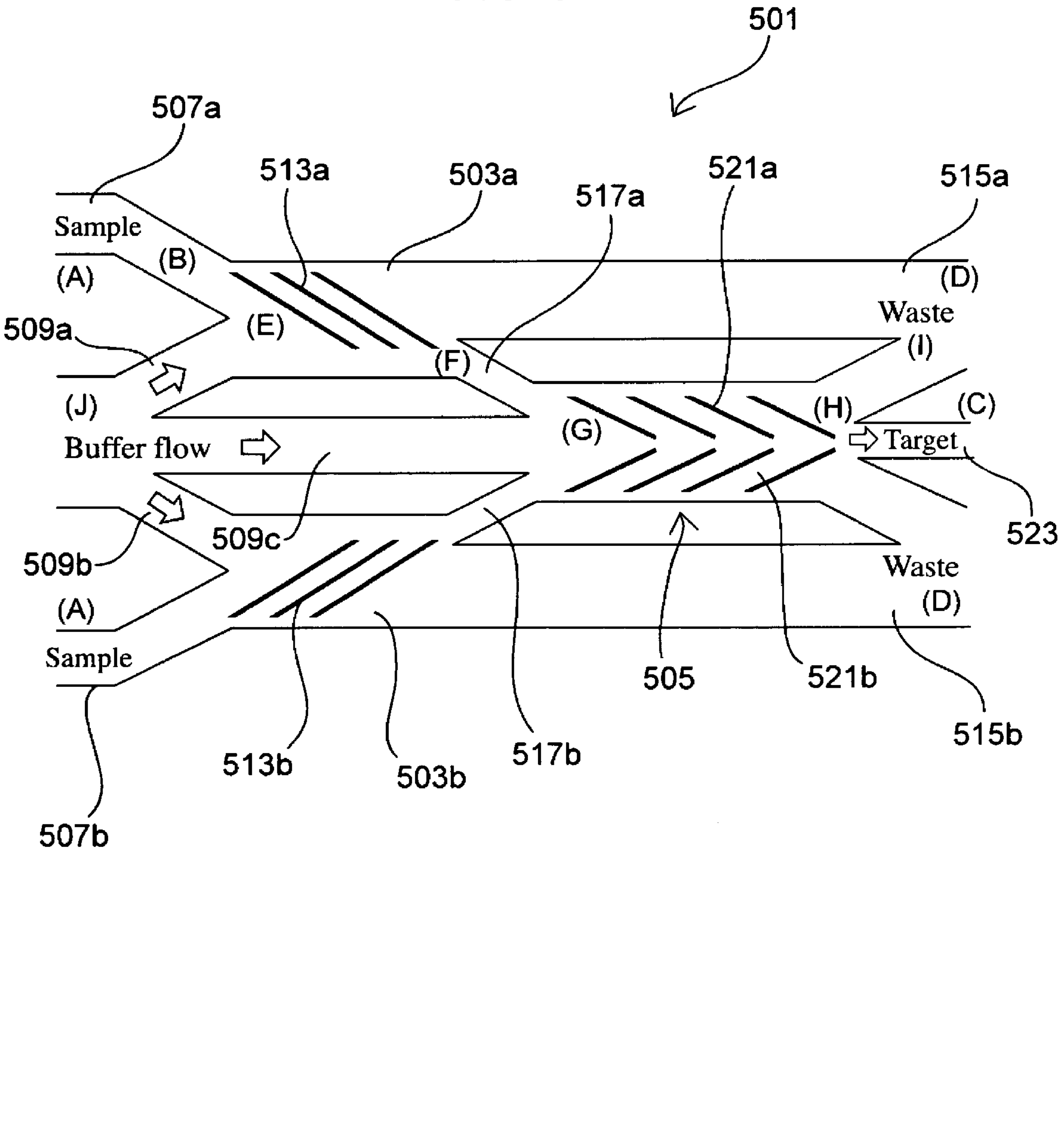
FIG. 5A is a schematic diagram of a multistage sorting structure in accordance with certain embodiments.

FIG. 5A presents one example of a microfluidics 501 device having at three MFG-based sorting stations: two parallel stations 503*a* and 503*b* being provided upstream of a third station 505 fed by both the parallel upstream stages. The hydrodynamics of the three-stage device is designed such that an inlet mixture of the sample is partitioned equally into the upper and lower inlet sorting channels 507*a* and 507*b* of the first stage, while the buffer solution is divided into three streams provided by channels 509*a*, 509*b*, and 509*c*. The streams remain laminar throughout the device due to their low Reynolds number. In the first stage, all cells flow through sorting stations 503*a* and 503*b* having MFGs 513*a* and 513*b* (location E), and flow pattern is designed such that, when the MFGs are not magnetized by an external field, all cells transported to waste outlet channels 515*a* and 515*b* (location D). When the MFGs are magnetized by an external field, the magnetically-labeled sample components are selectively deflected into the buffer stream via channels 517*a* and 517*b*. The selected cells from the first stage (location G) are then passed through the second sorting stage (station 505) having MFGs 521*a* and 521*b*, thereby further purging non-target components to provide a relatively high purity solution of target to a collection channel 523 (location C).

In one embodiment, the CMACS device of FIG. 5A is designed to prevent any backflow of fluid under the operating condition by ensuring that $P_{A,B}>P_E$, $P_F>P_G$, and $P_H>P_I$. Due to the fact that the device operates under laminar flow conditions—a regime well described by classical Poiseuille equations—the pressure drop $\Delta p$ in the channel is related to the volumetric flow rate Q where $$Q=\frac{wh^3\Delta p}{12\eta L}[1-O(h/w)]\approx\frac{wh^3\Delta p}{12\eta L}$$

and the flow resistance is given by $R=\Delta p/Q=12\,\eta L/wh^3$ where w, h and L are the width, height and length of the channel, respectively. As a first order approximation, a fluidic circuit model was created wherein each channel is represented by a resistor with unitless resistance $R'=L/w$. Subsequently the volumetric flow rate in each channel and pressure at each node may be solved using a commercial circuit simulator (e.g., PSpice, Cadence Design Systems, San Jose, Calif.) and the model may be refined by solving the Navier-Stokes equations for incompressible fluid with no-slip boundary conditions (e.g., FemLab, Comsol Ltd, Los Angeles, Calif.). The models may be used to simulate the pressure distribution in the microchannels to ensure that the particles will follow the streamline into the waste channel in the absence of magnetophoretic forces.

Fractionation

Fractionating cells based on their differences in surface protein expression level allows quantitative and/or qualitative characterization of cells based on surface protein expression level. In one application, one can detect and separate tumor cells from a heterogeneous cell population using certain defined prognostic markers for cancer. Fractionation may be used more generally to sort any sample based on degree of magnetization of various sample components. The central concept is that sorting does not have to be a "binary" undertaking. Rather, it can be a ternary or higher degree separation process.

Fractionating using magnetophoretic techniques can be understood in terms of the following cell-based example. The resultant magnetic force $\vec{F}_M$ on a cell depends on the expression level of target cells. This is because cells with more target expressed generally have greater numbers of magnetic particles coupled to them. The direction of the cells in flow is determined by a combination of the resultant magnetic force and the hydrodynamic viscous drag $\vec{F}_{VD}$. Using the design of an MFG, one can determine the deflection and average flow path of cells having differing levels of target expression. This allows the device design to precisely fractionate the cells by delivering different cells to multiple outlets.

Figure 5B:
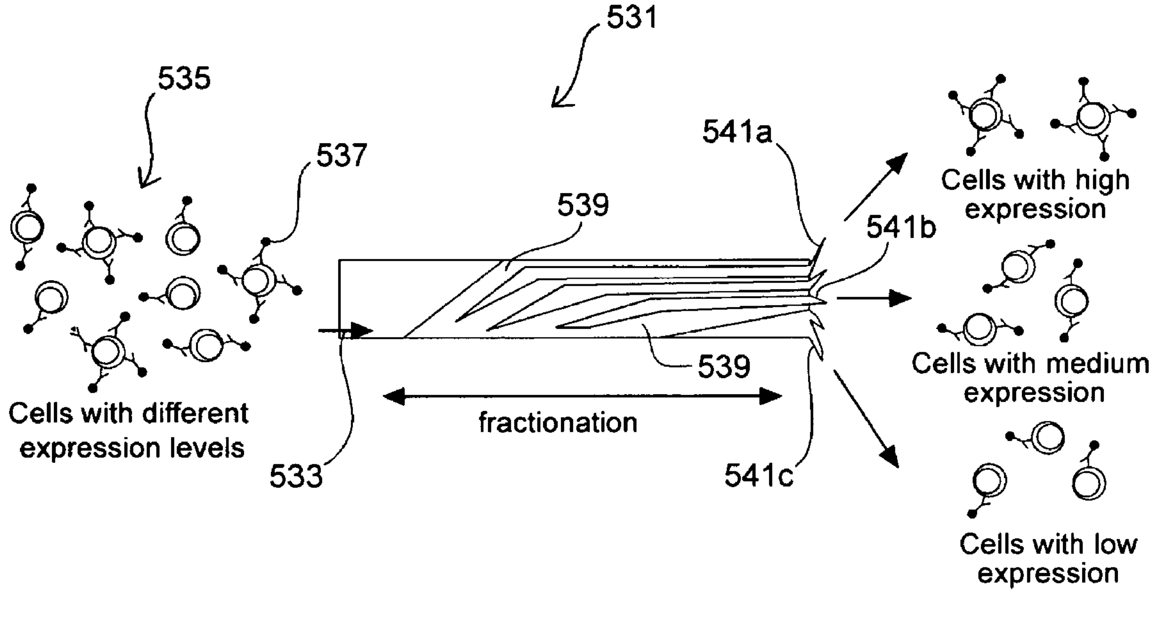
FIG. 5B is a schematic diagram of a fractionating sorting station.

A fractionating sorting station will employ one or more MFGs to generate the magnetic force, and multiple outlets to collect fractionated samples. FIG. 5B shows a fractionating sorting station 531. It includes, at the lower left side of the diagram, an inlet channel 533 for receiving magnetically tagged cells 535 with different levels of expression. The varying levels of expression are indicated by different numbers of coupled antibody-magnetic particle conjugates 537. Sorting station 531 includes multiple strip-type MFGs 539, each having a different angle with respect the direction of flow. In the depicted example, MFGs located upstream have steeper angles than MFGs located downstream. As shown, the MFGs possess a steady progression of decreasing angle in moving from the most upstream position to the most downstream position. A collection of parallel outlet channels 541 is positioned at the downstream side of fractionating sorting station 531. Cells deflected the most by the MFGs exit the "top" outlet channel 541*a*. Cells deflected the least exit the "bottom" outlet channel 541*c*, and cells deflected by an intermediate amount exit the "middle" outlet channel 541*b*. As can be seen in the figure, cells with a high level of expression can be collected from outlet channel 541*a*, cells with an intermediate level of expression can be collected from outlet channel 541*b*, and cells with a low level of expression can be collected from outlet channel 541*c*.

To verify the design of FIG. 5B, a numerical simulation was performed using COMSOL Multiphysics. In the Magnetostatics Model, nickel strips with 0.2 μm thickness, 40 μm width, and 40 μm separation distance are placed at the bottom of the device, and the magnetic field distribution and magnetic force are calculated. The simulation showed that magnetic field distribution is strongest at the edges of nickel strips.

A prototype fractionating sorting station was produced in which the MFGs were fabricated by electron-beam evaporation of 0.2-μm nickel thin film on borosilicate glass wafers after lithography and a lift-off process. Microfluidic ports were drilled into the glass substrates using a computer-controlled milling machine. Microfluidic channels were fabricated on a silicon wafer using a depp reactive-ion-etcher, which produced 35 μm deep channels. Polydimethylsiloxane (PDMS) replicas of the silicon master mold were fabricated by applying a precursor to the silicon master, followed by curing at 70° C. for 3 hours.

Figure 5C:
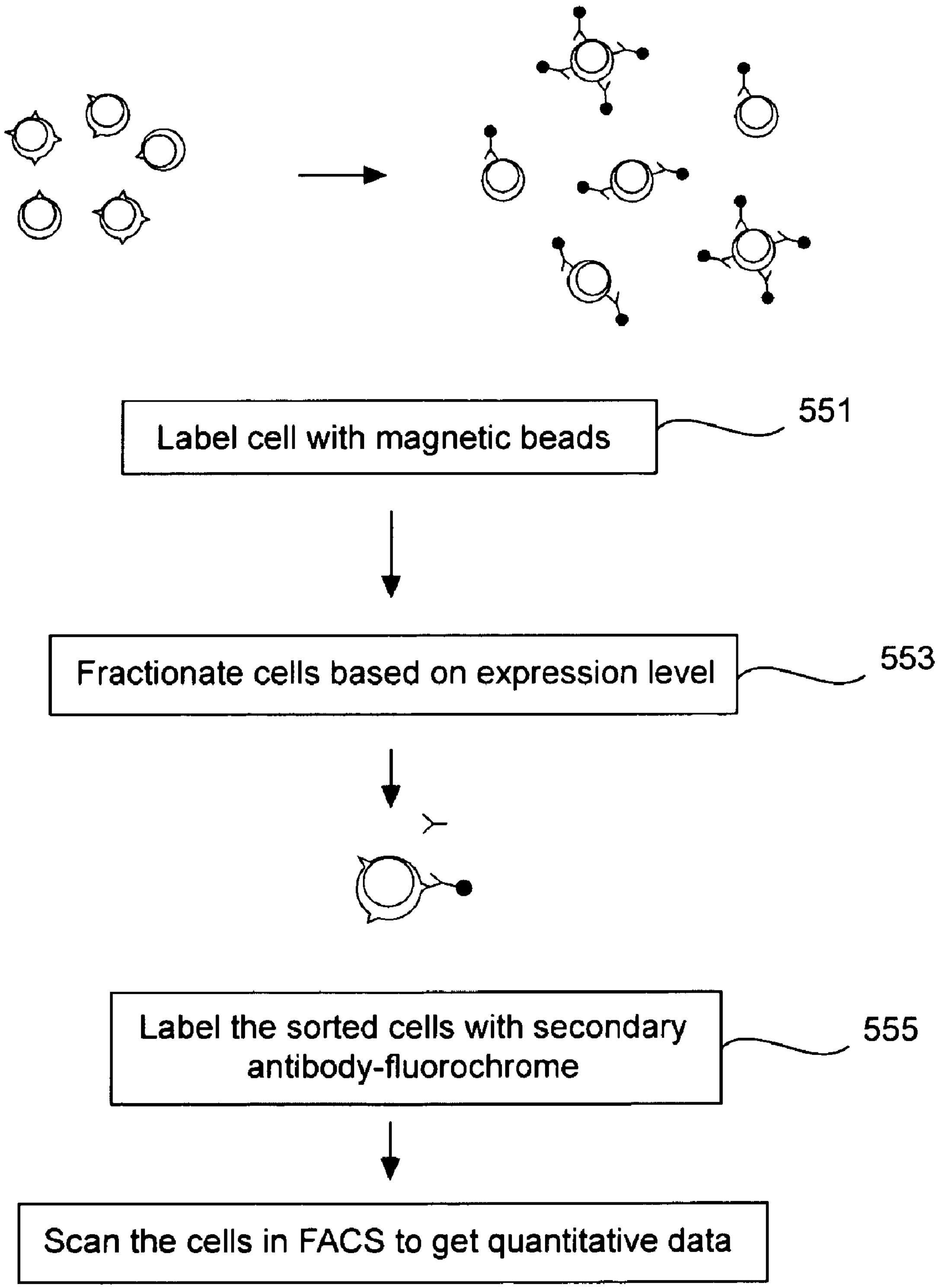
FIG. 5C is a flow chart of operations associated with a cell fractionating sorting device having an integrated cell detector.

To fractionate cell by surface protein expression level, a sequence of steps may be performed as shown in FIG. 5C. First, cells are labeled with magnetic beads (block 551). Second, the labeled cells enter a fractionation sorting station where they are sorted/fractionated (block 553). Next, the sorted cells are labeled with a secondary antibody-fluorochrome conjugate (block 555). Finally, the cells are analyzed using flow cytometry for quantitative data (block 557). Using the sorting station, the cells are fractionated based on their expression level and collected at multiple outlets.

In another example, cells or other species of interest may have two or more different types of markers (e.g., two different surface proteins or an antigen having two discrete epitopes). A sample suspected of harboring such species is treated with multiple different types of magnetic particles, one having an affinity for a first marker and another have an affinity for a second marker. Species having no markers will not be labeled. Species having only one marker will be labeled, but with only one type magnetic particle. Species having two markers will be labeled with two or more different types of magnetic particles. In a sorting station, the species having two more distinct markers will deflect to a greater degree than species having only one marker. Thus, a fractionating sorting station will be able to separately collect species with no markers, species with only marker, and species having multiple markers. Obviously, the idea can be extended to greater numbers of markers, three, four, etc.

Sorting Performance

The CMACS devices of this invention may be characterized by certain performance metrics. As indicated, these include at least (i) purity of the final target, (ii) throughput, and (iii) recovery. Obviously, the actual values and balance of these performance metrics depend on the goals of the application and the unique set of technical constraints imposed by the application. Still it is worth considering these parameters for comparison to other devices. Throughput refers to the number of analyte species (e.g., cells) that can be processed in a given amount of time. Purification refers to the purity of the purified target analyte collected from the microfluidics device. Obviously, this is strongly dependent upon the initial purity, the number of separation stages employed, etc. Note that in some embodiments, such as the one depicted in FIG. 5A, the multiple separation stages are integrated in a device or system. Each sequential separation stage will further purify the target. Finally, the recovery refers to the percentage of the target that is recovered. Typically, there will be losses but one advantage of the microfluidic devices disclosed herein is their ability to provide high recovery rates for rare species. In some examples, a lossless recovery may occur.

The values of these various parameters achievable using certain embodiments of the present invention will be presented here. As indicated, a target collected from a sorting device of this invention routinely achieves high purity. In one case, it was found that a CMACS device of this invention was capable of enriching a target by >10,000-fold in a single pass at a high throughput 1,000,000 particles/second/microchannel. Typical device designs sometimes have a throughput of at least about 10 microliters/hour/channel. In certain embodiments, the throughput is at least about 100 ml/hour/channel. Obviously, these throughput rates scale with the number of parallel channels in a device or system. Thus, for example, some five-channel devices may have a throughput of at least about 500 ml/hour.

The CMACS devices of this invention provide, in certain embodiments, recovery levels of rare components (e.g., rare cells) not previously achievable. In this context, recovery refers to the percentage of the target that is recovered. In some cases, the recovery rate is at least about 50%, even when sorting samples having a very low fraction of target (e.g., the initial concentration of target of about $10^{-5}$ or less target/total species (target and non-target)) and when operated at commercially reasonable throughput rates. In some embodiments, the recovery level reaches at least about 75% when sorting samples having an initial concentration of target of about $10^{-5}$ target/total species. It has also been found that sorting modules of this invention can recover at least 90% and even 100% of target in samples having initial concentrations of target of about $10^{-5}$ target/total species or less. In certain embodiments, these recovery rates can be achieved in samples having initial concentrations of target of about $10^{-6}$ target/total species or less, and in some cases in samples having initial concentrations of target of about $10^{-7}$ target/total species or less, Methods of Using Magnetophoretic Devices As indicated, the CMACS devices of this invention may be used in many different applications. Among these are recovering rare cells, screening molecular libraries, sorting magnetic materials in industrial settings, etc.

Figure 6A:
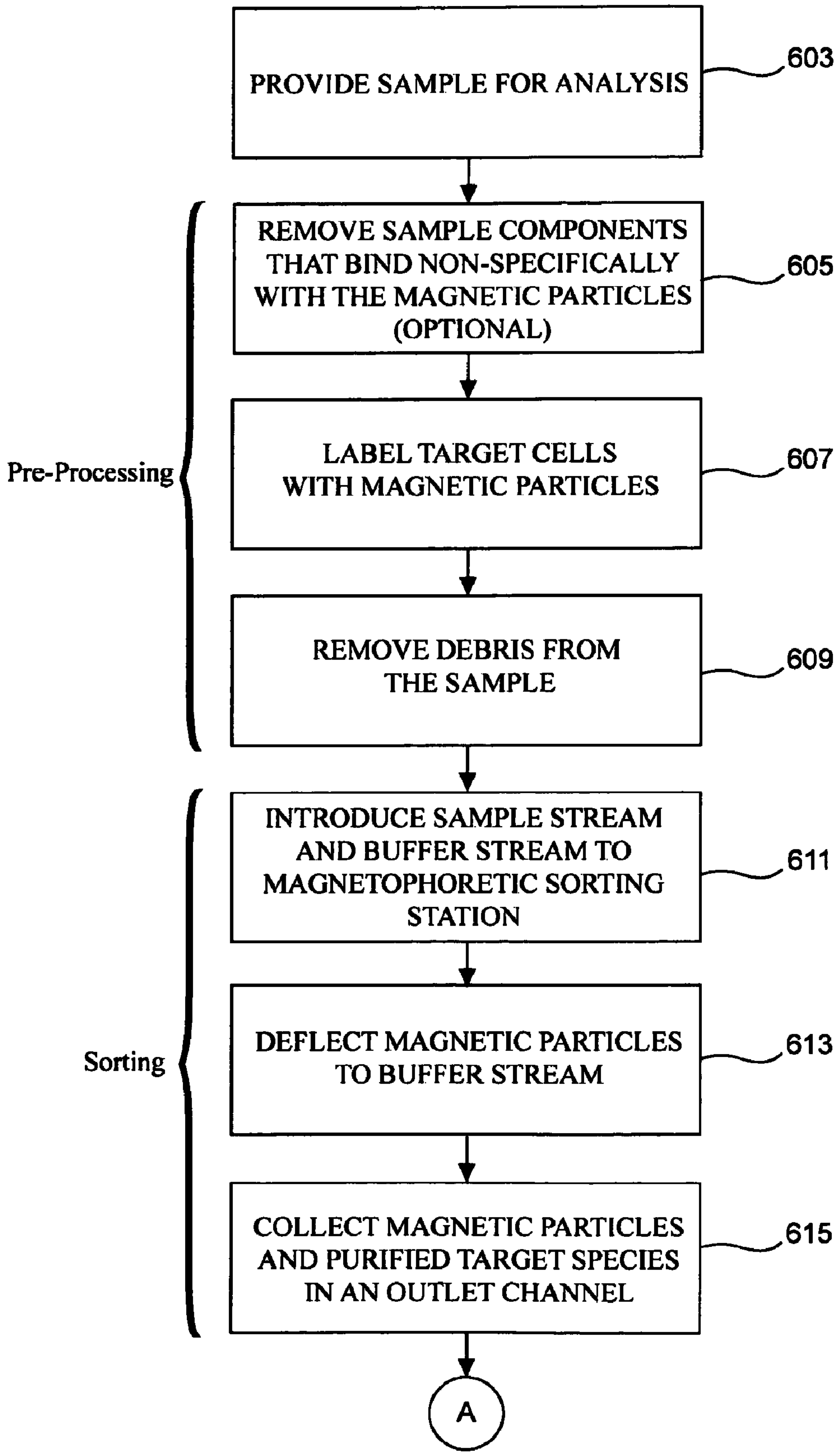
FIGS. 6A and 6B together constitute a process flow diagram showing a method of using a CMACS device in accordance with an embodiment of the invention.
Figure 6B:
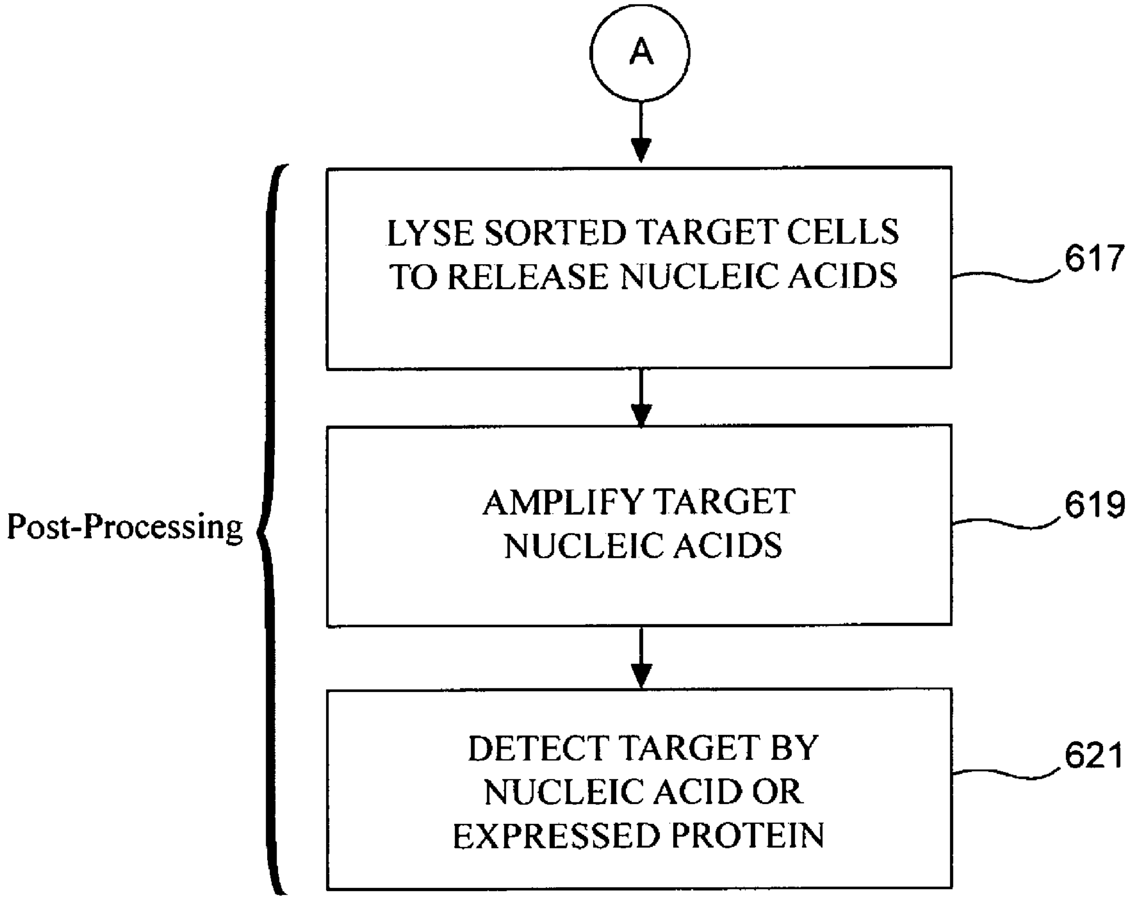

One general approach to using a CMACS device in accordance with an embodiment of the invention is presented in the flow chart of FIGS. 6A and 6B. As shown there, the process can be generally divided into a pre-processing stage, a magnetophoretic sorting stage, and a post-processing stage. Each of these stages may constitute one or more sub-stages. For example, as indicated in the discussion above a sorting device may include multiple magnetophoretic stages. In the example of FIGS. 6A and 6B, operations 605, 607, and 609 fall into the pre-processing stage, operations 611, 613, and 615 constitute the magnetophoretic sorting stage, and operations 617, 619, and 621 constitute the post-processing stage. In some embodiments, all or some of the pre-processing operations are performed on an integrated device or system that also includes the magnetophoretic sorting station(s).

In the depicted example, a target purification process begins with provision of a sample to be flowed through the CMACS device for sorting. See block 603. The term "sample" as used herein refers to a material or mixture of materials, typically, although not necessarily, in fluid form, containing one or more target species (e.g., biomolecules) of interest. If the sample is not already in liquid form it will be suspended, dissolved or otherwise incorporated in a liquid medium for delivery to a microfluidic sorting device. In certain embodiments, the sample is a physiological sample. The physiological sample may be a fluid or solid, where the solid may or may not be treated to render it fluid. Samples of interest include, but are not limited to: blood, serum, urine, plasma, sputum, as well as cell and tissue homogenates etc, from animal, plant and microbial sources. The sample may be pretreated as is desired and/or convenient, where pretreatment may include removal of particulate matter, viscous material, insoluble material, and the like. Optionally, sample components that bind non-specifically with the magnetic particles are removed in a sample pretreatment operation in which the sample is contacted with a pool of magnetic particles. See block 605. This optional process may be appropriate when, for example, the magnetic particles are coated with streptavidin or other moiety to which some sample components are reasonably likely to bind. After the magnetic particles and sample remain in contact for a period of time, the particles are removed from the sample by, e.g., a negative magnetophoretic operation. At least some of the non-specifically binding sample components will thereby be removed from the sample.

Next, the target species in the sample are labeled with magnetic particles. See block 607. Typically, this simply involves contacting the sample with magnetic particles that have been coated with an antibody or other capture moiety specific for the target, where the antibody or other capture agent has suitable binding affinity and specificity for the target species. In certain embodiments, the antibody or other capture moiety has an affinity for its target species of at least about $10^{-4}$ M, such as at least about $10^{-6}$ M and including at least about $10^{-8}$ M, where in certain embodiments the antibody or other capture moiety has an affinity for its target species of between about $10^{-9}$ and $10^{-12}$ M. In certain embodiments, the antibody or other capture moiety is specific for the target species, in that it does not significantly bind or substantially affect non-target species that may be present in the sample of interest. In some cases, the sample and magnetic particles may be contacted with a bifunctional reagent having one moiety that binds with a target species and another moiety that binds with the surface of magnetic particles. If the magnetic particles are coated with streptavidin for example, a suitable bifunctional reagent may be a biotinylated antibody specific for the target in the sample. Alternatively, one could directly modify surface of magnetic particles to immobilize entity having specific feature for binding with species of interest. Regardless of how the surface of the magnetic particle are modified, this process will allow the target to selectively bind to the magnetic beads. The concentration of beads is chosen based on the amount of target species expected to be present in the sample.

After the sample has been treated to effect labeling of the target species, the sample is optionally filtered or otherwise treated to remove debris that might clog device channels or otherwise interfere with the process. Examples of material that may be filtered from a sample includes coagulated sample materials, precipitates, etc.

Next, after incubation and optional filtering, the sample (with magnetic particles now labeling the target) is introduced as continuous flow to one or more inlets to magnetophoretic device. Simultaneously buffer solution is introduced to one or more other inlets to magnetophoretic device. See block 611. From this point, the sample flows past one or more magnetic field gradient generators in the device under conditions that cause magnetic particles to deflect into a buffer stream and toward an active material outlet. See block 613. The process optionally passes the through a second magnetic field gradient generator in the device—downstream from the first magnetic field gradient generator to effect further purification. Finally, the magnetic particles with purified target species are collected in an outlet channel. See block 615.

In the depicted process, the collected target (labeled with magnetic particles) is subjected to three separate post-processing operations. Each of these operations is described in greater detail elsewhere herein. In a block 617, a post-processing station lyses the collected target cells. In some embodiments, the lysis is conducted while cells are held stationary. This operation may be appropriate for analysis of pathogens such as bacteria for example. In some examples, the lysed pathogen provides components such as genetic material, particular organelles, or other characteristic biological or chemical components for detection. Next, as shown in a block 619, a further post-processing station optionally amplifies the contents of the lysed target to produce an increased signal of a target sequence of interest. Amplification is primarily relevant when particular genetic material is to be analyzed or detected. PCR or other known amplification techniques may be appropriate for this purpose.

In some embodiments, one or both of the lysis operation or the amplification will be unnecessary and the process is performed without one or both of them but with an additional detection operation as depicted at a block 621. In other embodiments, each of operations 617, 619, and 621 is performed in turn. Regardless of the exact sequence of post-processing operations, a detection station may detect the presence of the target via a microscopy, a fluorescent signature, a radioactive signal, etc. Examples of detection processes suitable for use with the invention include continuous flow processes such as various cell counting techniques or immobilization techniques such as microarray analysis.

Integrated CMACS Systems

As indicated above, various operational modules may be integrated in a microfluidics system, and in some cases on a single microfluidics chip. These modules may be sorting stages arranged in series and/or in parallel as depicted in FIGS. 1 and 5, for example. In addition, other modules or subsystems may be provided in a microfluidics system.

Figure 7A:
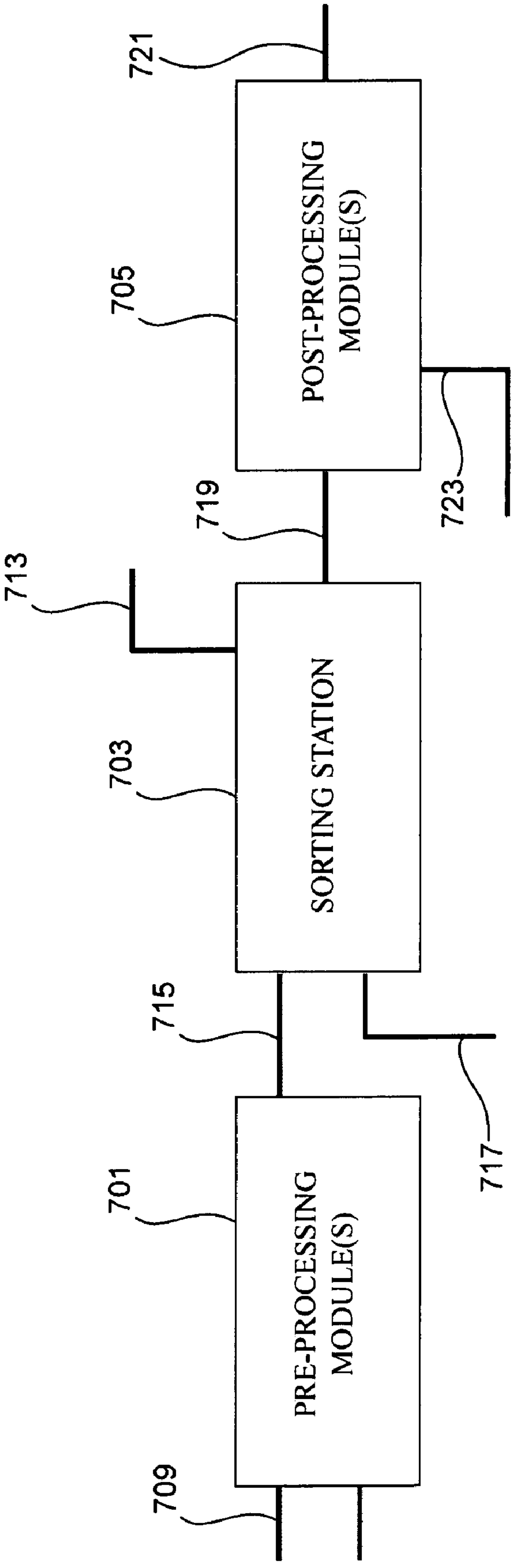
FIG. 7A is a generic depiction of a multi-module integrated microfluidics device or system in accordance with certain embodiments.

Further, as depicted in FIG. 7A, a microfluidics system may be designed with modules located upstream and/or downstream from the sorting station. The embodiment of FIG. 7A includes at least three general subsystems: a pre-processing subsystem 701, a sorting subsystem 703, and a post-processing subsystem 705. In some embodiments, two or all three of these subsystems are provided on a single device.

In the depicted embodiment, the pre-processing subsystem 701 includes a first inlet channel 709 for receiving the sample and one or more additional inlet channels (represented by second inlet channel 711). Depending on the design and application, these additional channels may be used to introduce magnetic particles, diluents, additives for tailoring rheological properties, etc. Pre-processing module 701 also includes an outlet channel 715 for providing labeled sample to the sorting subsystem 703. The pre-processing module 701 may optionally include one or more other outlets (not shown). As an example, the pre-processing subsystem may include modules or stations for filtering the sample, concentrating or diluting a sample, providing additives to adjust rheological properties of the sample, labeling the sample with the magnetic particles, disrupting sample components (e.g., lysis, viral protein coat disruption, etc.), and the like.

Typically, though not necessarily, sorting subsystem 703 will include one or more MFG-based sorting stations including at least a buffer inlet channel 717, a sample inlet channel 715, a waste outlet channel 713, and a collection channel 719 as described above. If a fractionation sorting module is employed, there will be multiple collection channels.

The post-processing subsystem 705 receives magnetically labeled target components via the collection channel 719. It expels processed fluids via an outlet channel 721. Subsystem 705 also optionally includes one or more inlets 723 for providing fluids necessary for effecting one or more post-processing operations (e.g., chemical lysing reagent or primers, nucleotides, polymerase, etc. for PCR). The post-processing subsystem may include modules for direct detection of the target via an appropriate detection technique, and it may optionally include additional pre-detection modules such as a lysis module or and amplification module as described herein. A detection module and any additional module may be implemented in one or more stations.

A controller is commonly employed to control the operations of an integrated microfluidics system. Algorithms implemented on a controller control the sequence and timing of flow to various modules through various ports, temperature cycling, application of magnetic and/or electric fields, and optical excitation and detection schemes, for example. While the controller is not shown or described extensively herein, one of skill in the art will understand that controllers may be employed with sorting modules and larger integrated systems herein. Controllers interpret signals from various sensors (if present) associated with the microfluidics device and provide instructions for controlling operations on the microfluidics system. All this is accomplished under the control of hardware and/or software logic, which may be implemented on a dedicated, specially designed microprocessor system or a specially configured general purpose computing system.

Figure 7B:
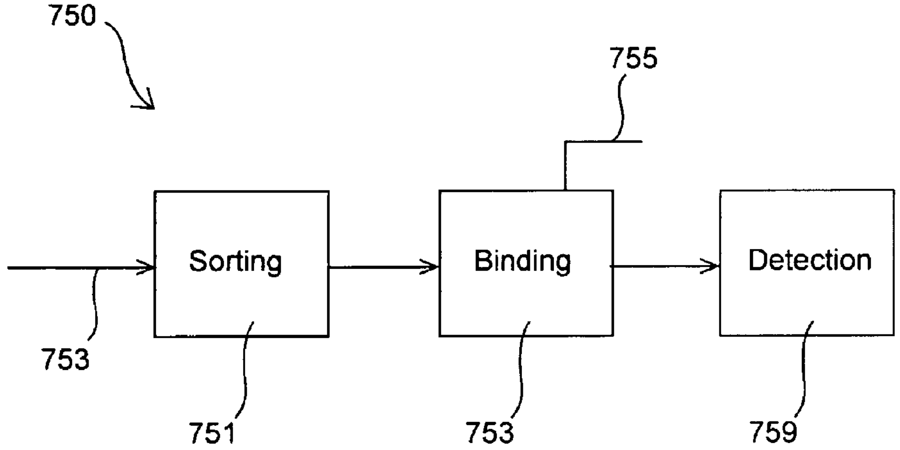
FIGS. 7B, 7C and 7D are block diagrams showing integrated devices or systems in accordance with various embodiments.

A few specific examples of integrated microfluidic systems will now be presented. In FIG. 7B, an integrated microfluidic system 750 is useful for identifying cells or other analyte components having at least two accessible target proteins. In this embodiment, a sample suspected of having a particular type of cell (e.g., a tumor cell) is provided to a sorting station 751 along with magnetic beads coated with an antibody to a first target on the tumor cell. These may be provided via an inlet channel 753. A separate buffer inlet may also be provided. After sorting the magnetically labeled tumor cells, they flow to a binding station 753 where fluorescently labeled antibodies to a second target on the tumor cells are delivered via an inlet channel 755. There, the antibodies come in contact with and bind to surface antigens on the tumor cells. The cells then flow to a detection module 759, where they are exposed to light of an excitation frequency for the fluorophore of the second antibody. Fluorescence detected on trapped cells indicates that the cells harbor both the first and second targets. This may be conclusive evidence that a particular type of tumor cell is present in the sample.

Figure 7C:
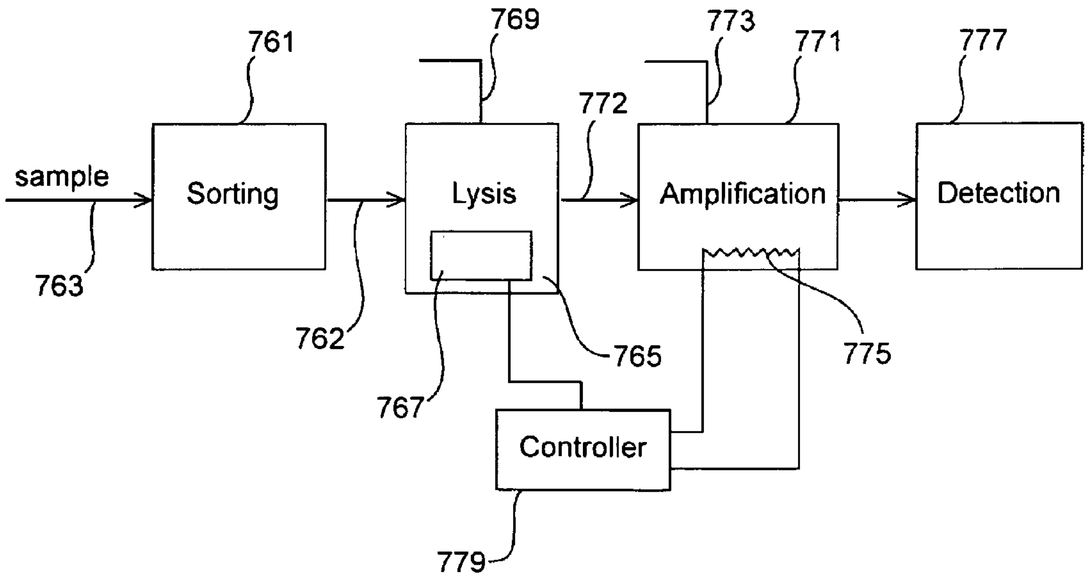

In FIG. 7C, a biological sample suspected of having a particular bacterial pathogen is introduced to a sorting station 761 via an inlet channel 763. In this example, it is assumed that the sample has been pre-labeled with magnetic beads coated with an antibody to a surface protein of the suspected pathogen. Such labeling may be accomplished off-chip or on-chip in a pre-processing module or station as indicated above. Sorting in station 761 separates the bacteria in question from other sample components. In the depicted embodiment, the magnetic beads (with attached bacteria if present) are delivered via a collection channel 762 to a lysis station 765 where a strong magnetic field is temporarily applied via a magnet 767 (permanent or electromagnet) to hold the magnetic beads stationary. Then a chemical lysing agent is introduced to lysing station 765 via an inlet 769. The lysing agent disrupts the bacterial membranes to release the genetic material, which is then free to pass out of the lysis chamber in a flow field to an amplification module 771 through a channel 772. In this module, nucleotide building blocks, primers, Taq polymerase, and buffer are provided via an inlet channel 773. Thermal cycling to drive a polymerase chain reaction in module 771 is controlled using a heating element 775. The bacterial DNA is thereby amplified while passing through module 771. It then passes out of the amplification module and enters a detection module 777 (e.g., a microarray), where it may be detected via a fluorescent signature. Alternatively, PCR may be conducted using a TaqMan™ oligonucleotide probe to enable fluorescent detection in detection module 777. Note that a controller 779 may be employed to control the timing of thermal cycling, the application of a magnetic field, etc. during operation.

Figure 7D:
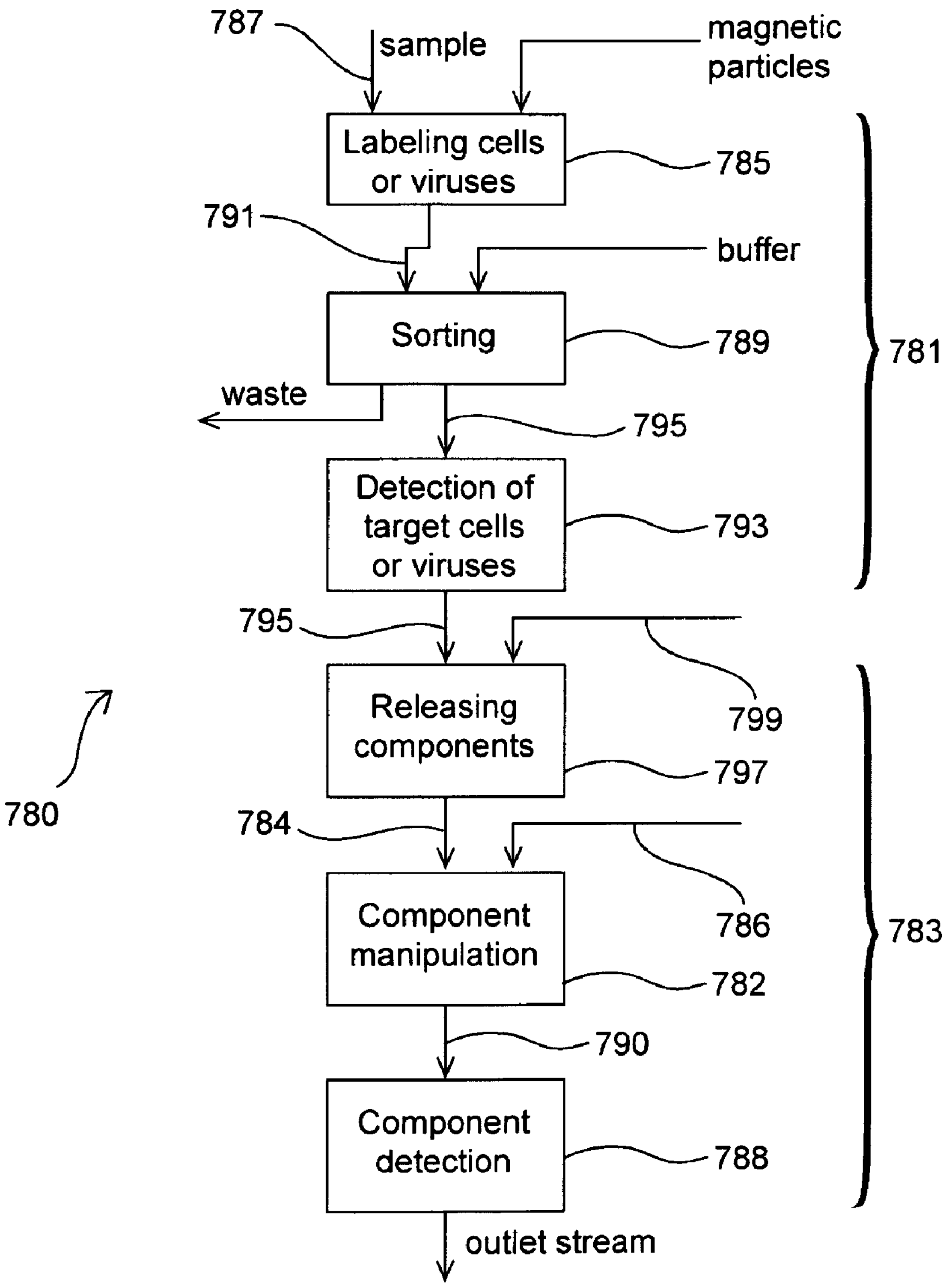

Certain embodiments employ two levels of detection, one for a first target species located on the surface of a cell or virus and a second for a second target associated with a component of the cell or virus. One example of an integrated device or system that may be employed for this purpose is depicted in FIG. 7D. In the depicted example, a first section of the device/system labels, separates and detects target cells or viruses from a sample. A second section then releases components of the cells or virus, which components are further manipulated by, e.g., amplification, and ultimately detected. Hence whole cells or viruses are first detected and then one or more components of the cells or viruses are separately detected. In some embodiments, the first target on the cell or virus is a surface protein, saccharide, or lipid. In some embodiments, the second target of the cell or virus is a nucleic acid or intracellular protein, saccharide, or lipid.

Turning now to FIG. 7D, a device or system 780 includes a first detection section 781 for detecting a cell or virus and a second detection section 783 for detecting a cell or virus component. Sections 781 and 783 are in fluid communication with one another. In detection section 781, a sample is provided a labeling station 785 via a sample inlet 787. In this station, the sample is contacted with magnetic particles which label cells or viruses having a first target on their membranes or protein coats. Labeled cells or viruses then flow to a sorting station 789 via an inlet 791. In station 789, buffer switching takes place under the influence of a magnetic field gradient in the manner described above. Cells or viruses harboring a surface target are thereby separated from other components of the sample and selectively delivered to a first detection station 793 via a channel 795. The cells or viruses are detected using fluorescence or other signature.

At this point in the device of system, the first level of detection has been completed and the cells or viruses are ready for the second level of detection, which is implemented in section 783. Initially, cells or viruses leave detection station 793 and flow via a channel 795 to a station 797 where the cells or viruses are disrupted in a manner that releases at least some of their components for further analysis. As explained elsewhere, the necessary disruption may be chemical, thermal, mechanical, acoustic, etc. as appropriate for the species of sample under analysis. In the depicted example, a separate inlet channel 799 provides reagent for disrupting the cell membrane or viral protein coat to release genetic material or other contents. In some embodiments, the cells or viruses are held stationary (at least temporarily) during treatment to release their components. The components released from the cell or membrane travel via a channel 784 from station 797 to a station 782, where the components are "manipulated" to facilitate further detection. The type of manipulation employed depends upon the type of component under consideration. For example, nucleic acids may be amplified in station 782 as described elsewhere herein. In other examples, subcellular components such as Golgi, cytoskeletal components, histones, mitochondria, etc. may be labeled with markers specific for those components (typically a biomolecule found within the component) in station 782. The markers, amplification reagents, or other component manipulation agent may flow into station 782 via an inlet channel 786. After appropriate manipulation in station 782, the components flow to a component detection station via a channel 790. There the component itself is detected by fluorescence, etc. as understood by those of skill in the art.

In some applications, loss of target species in a sample can lead to lack of commercial acceptance. Losses may be particularly problematic when the target is a rare cell species such as certain pathogens, tumor cells, stem cells, etc. As indicated, near 100% recovery of target species is sometimes desirable, even in cases where the initial concentration target in sample is extremely low (e.g., no greater than about $10^{-5}$ or even $10^{-7}$).

It has been found that often the most significant losses in microfluidic devices such as those described herein are in the delivery of the sample to the microfluidic devices. Particular problems occur when the sample passes through a pump or syringe when delivered to the device. In certain embodiments, losses are minimized by using designs in which the sample is not passed through a pump, syringe, or tubing prior to or during delivery to the sorting device. In a specific example, the microfluidic device includes an on-chip sample reservoir located upstream from the processing stations such as MFG sorting stations, labeling stations, detection stations, etc. In some cases, sample is preloaded in the reservoir and then consumed during processing in the device. For example, sample flow in the device may be actuated by applying pressure to the reservoir to drive sample out of the reservoir and into the remainder of the device. Using this approach, the sample need never contact a pump or tubing associated with the microfluidic device. Of course, the sample must be delivered to the reservoir prior to the sorting/separation process. Many low loss processes such as pipetting are available for this purpose and known to those of skill in the art.

Generally, the reservoir should be sized to hold sufficient sample to allow the sorting and any other processes to run to completion on the device. In specific examples, integrated devices such as those exemplified in FIGS. 7A-7D may employ an upstream sample reservoir as described here.

The nucleic acid amplification technique described here is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA).

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In order to effectively amplify nucleic acids from some pathogens or other target components, the microfluidics system may include a cell lysing or viral protein coat-disrupting module to free nucleic acids prior to providing the sample to an amplification module. Cell lysing modules may rely on chemical, thermal, and/or mechanical means to effect cell lysis. Because the cell membrane consists of a lipid double-layer, lysis buffers containing surfactants can solubilize the lipid membranes. Typically, the lysis buffer will be introduced directly to a lysis chamber via an external port so that the cells are not prematurely lysed during sorting or other upstream process. However, in some cases, the target to be sorted from a sample using labeled magnetic particles is only accessible after lysis. In such cases, it may be necessary to include a lysis module upstream from a sorting module. In such cases, the aim of lysis is to release the intracellular organelles and proteins for magnetophoretic separation processes. In cases where organelle integrity is necessary, chemical lysis methods may be inappropriate. Mechanical breakdown of the cell membrane by shear and wear is appropriate in certain applications. Lysis modules relying mechanical techniques may employ various geometric features to effect piercing, shearing, abrading, etc. of cells entering the module. Other types of mechanical breakage such as acoustic techniques may also yield appropriate lysate. Further, thermal energy can also be used to lyse cells such as bacteria, yeasts, and spores. Heating disrupts the cell membrane and the intracellular materials are released. In order to enable subcellular fractionation in microfluidic systems a lysis module may also employ an electrokinetic technique or electroporation. Electroporation creates transient or permanent holes in the cell membranes by application of an external electric field that induces changes in the plasma membrane and disrupts the transmembrane potential. In microfluidic electroporation devices, the membrane may be permanently disrupted, and holes on the cell membranes sustained to release desired intracellular materials released.

When the target is a virus or a component of a virus, it may be necessary to disrupt the viral protein coat at some stage in the microfluidic system. This may be done via thermal or chemical means as described for the lysis chamber, bearing in mind that different conditions may be required to remove or compromise a protein coat. In one example, the genetic contents of a virus are extracted by contact with an SDS (sodium dodecyl sulfate) solution. In certain embodiments, viruses coupled to magnetic particles are temporarily immobilized during sorting and/or extraction/separation of viral genetic materials.

As many viruses are retroviruses (their genetic material is RNA, rather than DNA), it may be necessary to perform reverse transcription in a microfluidic module prior to detection and/or amplification. Reverse transcription may be performed by implemented in a microfluidic module by delivering deoxyribonucleotides, primer, and a reverse transcriptase in a buffer at an appropriate temperature to cause the reverse transcription reaction to proceed. In some cases, reverse transcription and amplification may take place in a single module or station that employs all the necessary components for reverse transcription and amplification. In some embodiments, both processes are implemented by controlling the sequence of delivery of the appropriate nucleosides and enzymes to the station or module.

Many suitable detection techniques are available to detect target or other species in microfluidic modules employed in embodiments of the invention. These techniques may involve signals that are primarily optical, electrical, magnetic, mechanical, etc. A microfluidic detection module may employ continuous flow of the target or it may employ immobilized target as in the case of a nucleic acid microarray. In certain embodiments, fluorescent detection is employed. This of course requires that a fluorophore be coupled to the target species in or upstream from the detection module (unless the fluorophore is present in the native target as would be the cases with an expressed fluorophore such as a green fluorescent protein). In some embodiments, a detection module includes an inlet for receiving a fluorescently labeled antibody or other component specific for the target or a target associated feature such as a binding moiety on a magnetic particle or a particular protein on cell that carries the target. Presence of the fluorophore in the detection module is detected by exciting the molecule or moiety with light of an appropriate excitation frequency and detecting emitted light intensity at a signature emission frequency.

Many other detection techniques useful in a microfluidics environment are known to those of skill in the art. Examples include capacitive techniques, electrochemical techniques, mass detection techniques, and the like.

EXAMPLES

Example 1

Calculating a Balance of Forces on Magnetic Particles in the Device

To quantify the magnetic field gradient, Mathematica (Wolfram Research, IL) was utilized to obtain the magnetic field distribution around nickel stripes using an integral formula:

$$B(\vec{r}) = -\frac{\mu_0}{4\pi}\int\frac{\vec{M}(\vec{r})\cdot\vec{n}}{|\vec{r}-\vec{r}_0|^3}(\vec{r}-\vec{r}_0)dA$$

where $\vec{M}(\vec{r})$ is the magnetization of the nickel strip, and $\vec{n}$ is the unit normal vector on the surface. In our device, the width and thickness of each stripe was 20 μm and 0.2 μm, respectively, with the gap between adjacent stripes of 20 μm. It was assumed that the external magnet (NdFeB) magnetized the nickel stripes to saturation, at the internal magnetization of 6,000 Gauss for nickel, along the horizontal direction. Although the magnetic flux density from the MFGs is not as strong compared to the surface of the external magnet, the gradient of the magnetic field is very large within a few microns of the line edges (see FIG. 2). As a result, the MFGs allow precise shaping of the field distribution in a reproducible manner inside microfluidic channels. Once the B-field gradient is established, the physical separation between the labeled and unlabeled bacterial cells (or other sample component) occurs through the balance between hydrodynamic and magnetophoretic forces. The simulation results indicated a magnetic field gradient >5000 T/m within 1 μm from the edge of the MFGs.

Example 2

Application of a CMACS Device to Screen a Molecular Library

In this example, a CMACS device was employed to perform magnetophoretic screening of a molecular library in a microfluidic device. Specifically, a $10^8$-member peptide library was screened to identify a consensus sequence of amino acids with affinity towards the target protein (α-FLAG M2 monoclonal antibody).

The bacterial strains used in this work displayed peptides as insertional fusions into the second extracellular loop of outer membrane protein OmpX of *E. coli*. Streptavidin-coated superparamagnetic microbeads were purchased from Dynal Biotech (M280, Carlsbad, Calif.). Streptavidin R-phycoerythrin was obtained from Molecular Probes (Carlsbad, Calif.), and the biotinylated anti-FLAG M2 antibody was obtained from Sigma.

Micro-magnetic field gradient generators (MFG) were fabricated by electron-beam evaporation of 200-nm nickel on borosilicate glass wafers after an optical lithography and a lift-off process. This involved a blanket deposition a photoresist on the glass wafer, followed by optical exposure to the MFG pattern, development of the resist, and deposition of the nickel by evaporation from a nickel target. Microfluidic vias of diameter approximately a few hundred micrometers were drilled into the glass substrates using a computer-controlled CNC mill (Flashcut CNC, Menlo Park, Calif.). The negative-tone master mold of the microfluidic channels was fabricated on a 4-inch silicon wafer using a deep reactive-ion-etcher (SLR-770, Plasmatherm, St. Petersburg, Fla.), which produced 50 μm deep channels. Subsequently, the PDMS replicas of the silicon master mold were fabricated by applying a precursor (Sylgard 184, Dow-Corning Inc., Midland, Mich.; 10 part base resin: 1 part curing agent) to the silicon master, followed by curing at 70° C. for 3 hours. After dicing the borosilicate glass wafers, the MFC substrate and the PDMS channel were cleaned in acetone and oxidized in a UV-ozone chamber prior to their covalent bonding in a flip-chip aligner (Research Devices M8A, Piscataway, N.J.). Microfluidic inlets and outlets were attached to the device with epoxy. Each CMACS device was only used once and discarded after each usage to eliminate contamination.

A two stage CMACS device was utilized to screen a peptide library displayed on the surface of *E. coli* to isolate the consensus sequence of amino acids that exhibit high affinity binding towards the target molecule (anti-FLAG BioM2 mAb, Sigma). Since the target antibody is biotinylated it binds strongly to streptavidin, and as such, the *E. coli* clones displaying peptides with affinity for the antibody binding pocket (or affinity for streptavidin directly) become bound to the streptavidin-coated magnetic beads.

Figure 8:
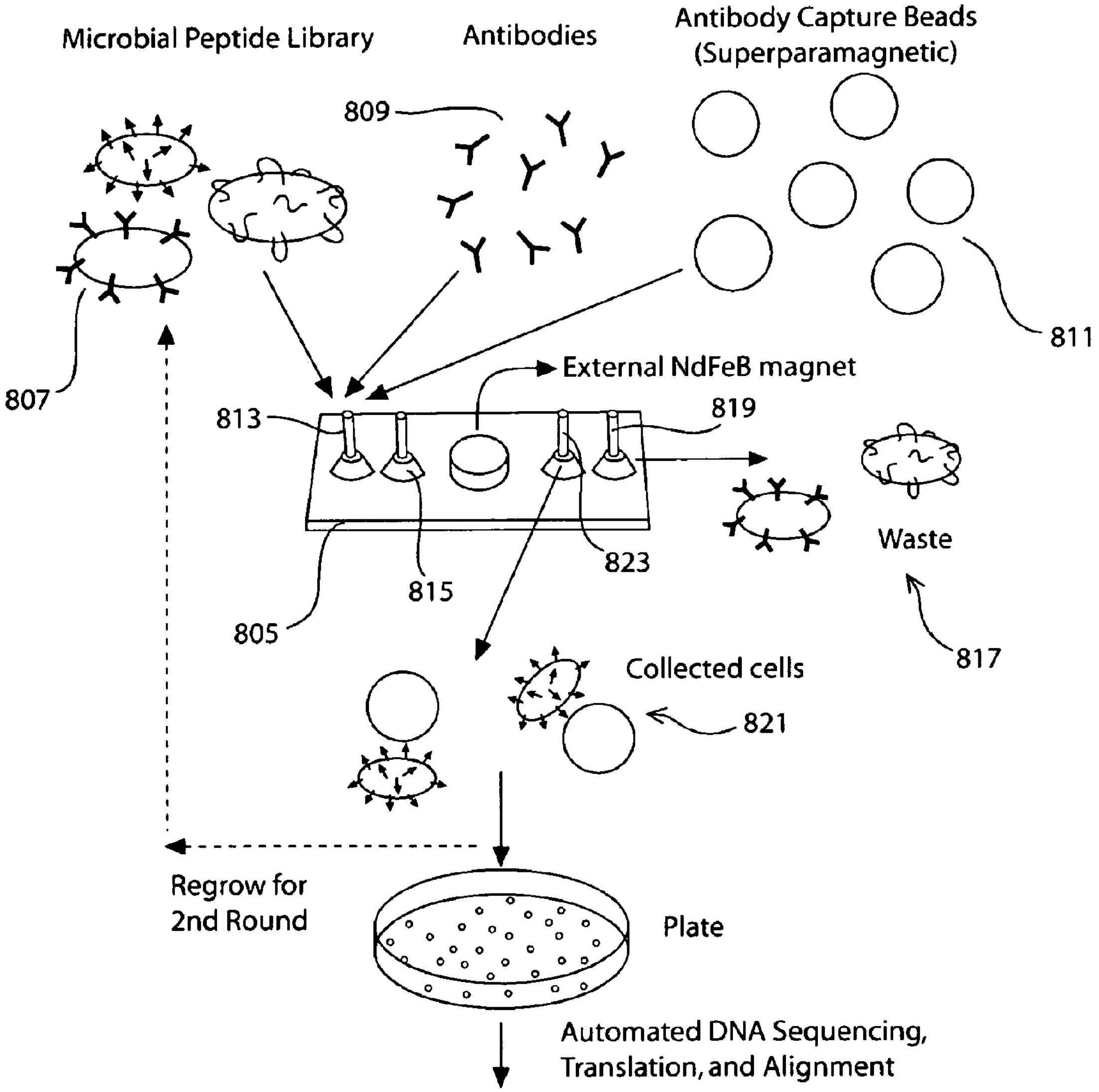
FIG. 8 is a schematic diagram of a peptide library screening and epitope mapping example using a microfluidic sorting device. Bacterial cells displaying peptides complementary to the antibody-binding region are captured on superparamagnetic beads, allowing continuous-flow separation by magnetophoresis. The binding population is then either amplified by growth for a further round of labeling and sorting, or plated on solid media to isolate single clones for sequence determination.

In this example, the bead-captured clones were sorted from the non-binding cells using a two-stage CMACS device 805 as depicted in FIG. 8. A bacterial peptide library 807, antibodies 809, and superparamagnetic beads 811 were all provided to a sample inlet port 813 in device 805. Buffer was provided through an inlet port 815. A waste stream containing non-binding library members 817 exited via a port 819. Target cells 821 labeled with the magnetic beads were provided via a collection stream from a port 823.

Prior to delivering the library to CMACS device 805 for positive screening, the initial peptide library (500 μL of cells at $2\times10^9$ cells/mL) was de-enriched for streptavidin (SA) binders by incubating with SA-coated magnetic beads ($4\times10^7$ beads/mL) and negative CMACS selection. Next, the remaining cells were incubated with biotinylated target protein (α-FLAG M2 monoclonal antibody) at a final concentration of 5 nM at 4 C for 1 hour, washed twice in PBS, and incubated with magnetic beads at a concentration of $4\times10^7$ beads/mL for positive CMACS screening.

To reduce settling of the beads during CMACS screening, the density of the solution was adjusted to that of polystyrene beads (1.06 g/ml) by adding glycerol at a final concentration of 20% (vol/vol). Microfluidic interconnections were provided by Tygon tubing (inner diameter of 0.02 inches, Fisher Scientific), which was attached to the inlets and outlets of the device. A pair of NdFeB magnets (5 mm in diameter, K&J magnetics, Jamison, Pa.) was attached to the top and bottom side of the device to externally magnetize the MFGs. The locations of the paired magnets with respect to MFGs were adjusted under a microscope to optimize the sorting performance.

A dual-track programmable syringe pump setup (Harvard Apparatus Ph.D. 2000, Holliston, Mass.) delivered both the cell mixture and the sorting buffer into the device at a constant flow rate. The device and the tubing were filled with sorting buffer (1×PBS/20% glycerol/1% BSA) to drive out air bubbles before pumping. The volumetric sample flow rate during sorting was 500-1000 μL/hour, and the buffer flow rate was 2-4 times that of sample flow. The flow of the beads in the microchannel was monitored through an upright, bright-field microscope (DM 4000, LEICA Microsystems AG, Wetzlar, Germany) and a cooled CCD camera (ORCA-AG, Hamamatsu corporation, Bridgewater, N.J.). The enriched cell solution was collected in a microcentrifuge tube. The collected enriched cells were amplified by overnight growth in LB medium with 0.2% glucose. A second round of induction, labeling, negative CMACS depletion of SA binders, positive CMACS enrichment of target binders, and overnight growth was performed at a reduced cell concentration of $10^8$ cells/mL and $10^7$ beads/mL.

Figure 9:
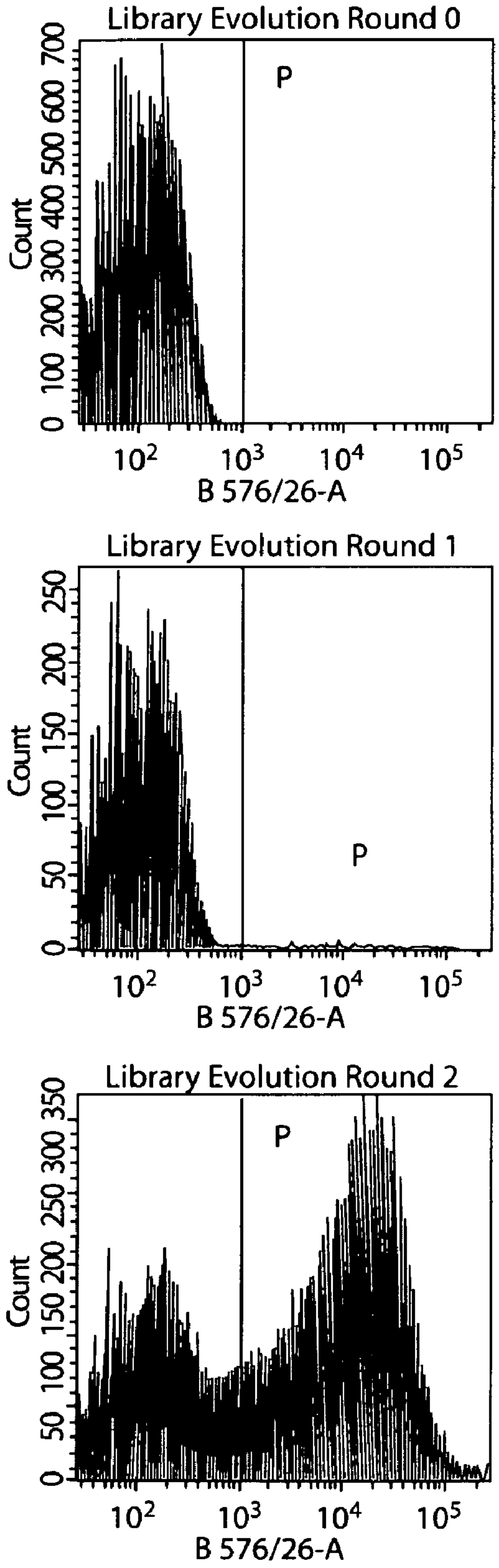
FIG. 9 is a series of three graphs showing results of flow cytometric analysis of the CMACS selection: A peptide library was incubated with biotinylated target and subsequently with streptavidin-coated magnetic beads. The library was screened with CMACS for target-binding peptides and the screened clones were amplified overnight. The fraction of target-binding population in the library was analyzed by flow cytometry after incubating them with fluorescently labeled target.

The initial frequency of cells that express target-binding peptides was quantified using flow cytometry after labeling the library with biotinylated target antibody conjugated with a fluorophore (SAPE). This measurement gave the combined frequency of target-binding peptides as well as unwanted subpopulation that simply binds to streptavidin on the magnetic beads. The frequency of SA-binding peptides was independently measured by incubating the library with SAPE. The difference of the two measurements gave the net frequency of target-binding population. Before CMACS, the frequency of target-binding cells was 0.03% (FIG. 9 top). After the first round of screening, the frequency of target cells reached 0.7% (FIG. 9 middle) and the second round enriched the target cells to 53.6% of the population (FIG. 9 bottom).

Note that FIG. 9 provides flow cytometric analysis of the CMACS selection. The fraction of target-binding population in the library was analyzed by flow cytometry after incubating them with fluorescently labeled target. The intensity of red fluorescence (x-axis) indicates the expression level of target-binding peptides on each cell. (a) Unselected library (b) Following one round of CMACS, 0.7% of the population exhibit target-binding peptides (c) 23.8% of the population exhibit target-binding peptides after two rounds.

Following the screening, the collected fraction was diluted and spread on agar plates to obtain colonies. Colonies were picked to individual wells of a 96-well microtiter plate, grown overnight in LB medium with 25 ug/ml chloramphenicol and 0.10% (v/v) glycerol, and then frozen. Template preparation and plasmid sequencing were then carried out by the High-Throughput Genomics Unit (HTGU), Department of Genome Sciences at the University of Washington.

Cell library population analysis was performed with conventional FACS (FACSAria, BD Biosciences, San Jose, Calif.), which was carried out by growing, inducing, and labeling the library with biotinylated anti-FLAG antibody at a final concentration of 5 nM. The cells were then washed twice and incubated on ice with streptavidin-phycoerythrin (60 nM) for 45-60 min. Cells were washed once and resuspended in cold PBS at a final concentration of ~$10^6$ cells/mL and immediately analyzed by flow cytometry. Control samples were prepared in parallel with SAPE labeling, but without antibody labeling, to assay SA binding clones.

A total of 87 sequences were obtained from clones isolated in the second round of sorting. The sequences were aligned using the program AlignX (Invitrogen, Carlsbad, Calif.) employing the ClustalW algorithm. A clear consensus group (21 of 87) contained a strong motif of DYKxxD, the well-established critical motif of the FLAG epitope. The identification of the consensus motif validates the methodology of CMACS based epitope mapping. It is also apparent that the streptavidin binding clones were co-enriched and abundant, however, they are easily identified and excluded from the pool of sequences at the data analysis stage because they present the known HPQ or HPM motif (31 of 87 sequences), as well as other known disulfide-constrained motifs (4 of 87). The remaining sequences displayed no consensus, most likely originating from non-specific binding during the screening process. The sequence analysis is in qualitative agreement with the enrichment factors as monitored by flow cytometry.

Example 3

Parallel Architecture

In order to achieve higher throughput, the use of parallel branch architecture can be used. This example presents a three-dimensional "channel circuit."

In the example, multiple channels are fabricated in one chip. The microchannel design is optimized to achieve a uniform flow pattern in each of multiple sorting stations. One challenge in implementing a three-dimensional channel circuit is the fact that flow streams may have to cross each other to achieve the necessary routing. To address this challenge, multiple layers for fluid distribution are used, analogous to an over-pass in a highway, where the buffer is introduced and divided into several sub streams in one layer, while the sample is introduced and infused into several downstream channels in another layer. This way, only two microfluidic connections are required at the inlet.

In this example, the channels are 20 μm deep and about 1 mm wide, which means that the flow should always be fully developed laminar flow. One goal of this example is to design the channel structure so that the same flow pattern results in every single channel. With a relatively wide inflow channel, one can achieve the same flow velocity and distribution in each channel. Generally this means that the fluidic resistance in the branches should be significantly greater than of the trunk or parent branch, typically on the order of at least 10× greater and sometimes in the range of 100× greater.

Figure 10A:
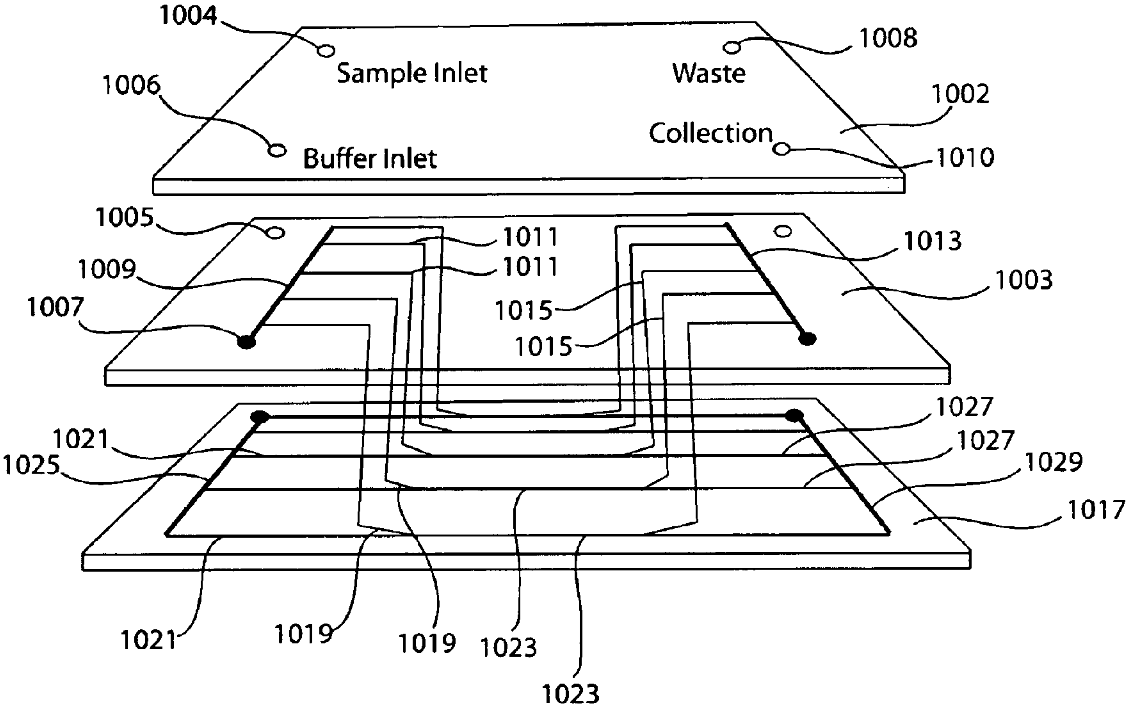
FIGS. 10A and 10B are diagrams showing a multilayer buffer switching sorting device having multiple sorting devices operating in parallel.

In an embodiment 1001 depicted in FIG. 10A (a schematic view), a top layer 1002 includes a port 1004 for sample inlet, a port 1006 for buffer inlet, a port 1008 for waste outlet, and a port 1010 for collection outlet. Underlying top layer 1002 is a layer 1003 that includes a sample inlet 1005, a buffer inlet 1007. Sample inlet 1005 allows sample to pass through layer 1003 to an underlying layer having features for distributing sample into multiple streams. Layer 1003 also includes a channel 1009 for distributing buffer into multi stream channels 1011 that direct the buffer to parallel sorting stations on a lower level. Layer 1003 further includes a channel for collecting the target collection from multiple collection stream channels 1015 from the sorting stations. A lower layer 1017 includes buffer inlets 1019 and multiple channels 1021 for distributing sample to multiple sorting stations 1023. The sample channels 1021 receive sample distributed from a main sample channel 1025, also located on lower layer 1017. The main sample channel provides a central connection with the sample inlet port 1004. Multiple waste outlet channels 1027 for receiving waste streams from the sorting stations are also provided on layer 1017. Finally, a main waste collection channel 1029 is provided on layer 1017 for providing a central contact with waste port 1008 on the top layer.

To analytically model this approach, the flow field of a device with five channels was modeled in FEMLAB 3.1 (Comsol). During the simulation the width of inflow channel and distance between each sorting station was optimized. The flow field was calculated with an incompressible Navier-Stokes equation and the fluid properties were set to be aqueous. The steady state velocity field in each sorting station was shown to be nearly identical.

Figure 10B:
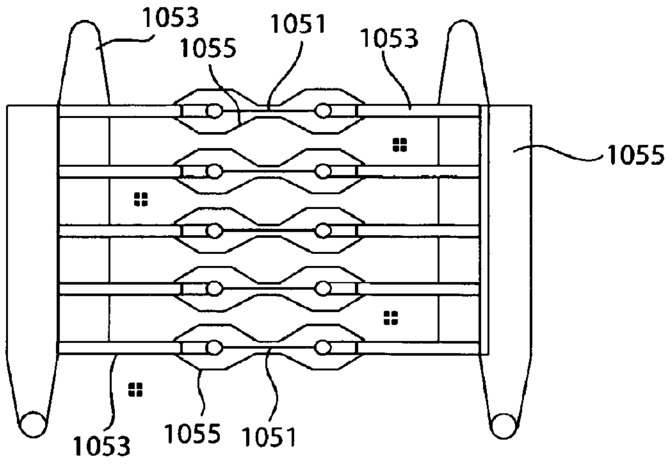

FIG. 10B shows a mask layout of a prototype parallel CMACS design in which a "red" layer shows nickel magnetic field gradient generators 1051, a dark layer showing channels 1053 in a top fluidic layer and a light layer showing channels 1055 in a bottom fluidic layer.

Other Embodiments

A number of embodiments of the invention have been described. Nevertheless, it will be understood that various modifications may be made without departing from the spirit and scope of the invention. For example, while a continuous processing/screening mode has been described, other techniques such as batch sorting may be employed in some embodiments. Further, the above description has been focused on biological applications and in particular cell sorting, but it should also be noted that the same principles apply to other sample types, such as inorganic or non-biological organic materials. Thus, the apparatus and methods described above can also be used to sort non-biological substances. Accordingly, other embodiments are within the scope of the following claims.

What is claimed is:

1. A microfluidic sorting device comprising:

(a) at least one inlet channel configured to provide separate streams of (i) a sample comprising a target species, non target species, and magnetic particles having an affinity for the target species in the sample, and (ii) a buffer that is substantially free of the sample;

(b) a sorting station fluidly coupled to said at least one inlet and located in a path of the sample stream;

(c) a magnetic field gradient generator for interacting with an external magnetic field to produce a change in magnetic field gradient in the sorting station and thereby deflecting the magnetic particles toward the buffer stream, and wherein the magnetic field gradient generator comprises a plurality of ferromagnetic elements comprising ferromagnetic strips arranged in an angled configuration where the first ends of two ferromagnetic strips in the angled configuration touch or are separated by a first distance and the second ends of the two ferromagnetic strips are separated by a second distance, the second distance being greater than the first distance; and (d) at least one outlet channel configured to separately receive the buffer stream with deflected magnetic particles and a waste stream containing said sample at least partially depleted of the target species.

2. The microfluidic sorting device of claim 1, wherein the at least one inlet channel comprises a first inlet channel for providing at least a portion of the buffer stream and a second inlet channel for providing at least a portion of the sample stream.

3. The microfluidic sorting device of claim 1, wherein the at least one inlet channel comprises (i) a first inlet channel for providing the buffer stream, and (ii) a second inlet channel and a third inlet channel for providing separate streams of the sample.

4. The microfluidic sorting device of claim 3, wherein the second and third inlet channels are located on opposite sides of the first inlet channel, such that, during operation, the buffer stream enters a sorting station straddled by 2 sample streams.

5. The microfluidic sorting device of claim 1, wherein the magnetic field gradient generator comprise a plurality of ferromagnetic elements are patterned on the sorting device proximate the sorting station.

6. The microfluidic sorting device of claim 5, further comprising a permanent magnet proximate the plurality of ferromagnetic elements.

7. The microfluidic sorting device of claim 6, comprising two permanent magnets located on opposite sides of the plurality of ferromagnetic elements.

8. The microfluidic sorting device of claim 5, further comprising an electromagnet proximate the plurality of ferromagnetic elements.

9. The microfluidic sorting device of claim 5, wherein the plurality of ferromagnetic elements are disposed within a fluid pathway of the sorting station to allow fluid contact between the ferromagnetic elements and the sample stream.

10. The microfluidic sorting device of claim 5, wherein the ferromagnetic elements are micropatterned nickel elements.

11. The microfluidic sorting device of claim 5, wherein the plurality of ferromagnetic elements comprises one or more pins or pegs.

12. The microfluidic sorting device of claim 1, wherein the sorting device comprises at least two magnetic field gradient generators.

13. The microfluidic sorting device of claim 12, comprising fluid paths for two separate sample streams positioned on opposite sides of a fluid path for the buffer stream, wherein the at least two magnetic field gradient generators are located in the fluid paths for the two separate sample streams on opposite sides of the fluid path for the buffer stream.

14. The microfluidic sorting device of claim 12, comprising two permanent magnets shared by the at least two magnetic field gradient generators.

15. The microfluidic sorting device of claim 1, wherein the at least one outlet channel comprises: (i) a first outlet channel for collecting at least a portion of the buffer stream comprising purified target species; and (ii) a second outlet channel for collecting at least a portion of the sample stream.

16. The microfluidic sorting device of claim 15, wherein the second outlet channel is sized and positioned to collect a separate portion of the buffer stream.

17. The microfluidic sorting device of claim 1, wherein the at least one outlet channel comprises: (i) a first outlet channel for collecting at least a portion of the buffer stream comprising purified target species; and (ii) a second outlet channel and a third outlet channel for collecting separate streams of the sample.

18. The microfluidic sorting device of claim 17, wherein the second and third outlet channels are located on opposite sides of the first outlet channel.

19. The microfluidic sorting device of claim 1, wherein the magnetic field gradient generator is configured to temporarily capture the magnetic particles and then release said magnetic particles to the at least one outlet channel.

20. A microfluidic sorting device comprising:

(a) at least one inlet channel configured to provide separate streams of (i) a sample comprising magnetic particles and non-magnetic particles, and (ii) a buffer that is substantially free of the sample;

(b) a sorting station fluidly coupled to said at least one inlet and located in a path of the sample stream;

(c) a magnetic field gradient generator for interacting with an external magnetic field to produce a change in magnetic field gradient in the sorting station and thereby deflecting the magnetic particles toward the buffer stream, wherein the magnetic field gradient generator comprises a plurality of ferromagnetic elements comprising ferromagnetic strips arranged in an angled configuration where the first ends of two ferromagnetic strips in the angled configuration touch or are separated by a first distance and the second ends of the two ferromagnetic strips are separated by a second distance, the second distance being greater than the first distance; and (d) at least one outlet channel configured to separately receive the buffer stream with deflected magnetic particles and a waste stream containing said sample at least partially depleted of the magnetic particles.

21. The microfluidic sorting device of claim 1, further comprising a cell lysis module.

22. The microfluidic sorting device of claim 21, wherein the cell lysis module is disposed downstream of the sorting station.

23. The microfluidic sorting device of claim 1, wherein the plurality of ferromagnetic elements has an orientation that is neither parallel nor perpendicular to the buffer stream's direction of flow in the sorting station.

24. The microfluidic sorting device of claim 1, wherein the plurality of ferromagnetic elements are arranged on the sorting device to direct the magnetic particles in a downstream direction that is not in the magnetic field gradient's direction nor in the sample stream's direction of flow.

25. The microfluidic sorting device of claim 1, wherein the plurality of ferromagnetic elements comprises a first set of ferromagnetic elements positioned in a symmetrical, opposing relationship relative to a second set of ferromagnetic elements.

26. The microfluidic sorting device of claim 1, wherein the magnetic field gradient generator comprises a plurality of ferromagnetic elements disposed within the sorting station to allow fluid contact between the ferromagnetic elements and the sample stream.

27. The microfluidic sorting device of claim 21, wherein the cell lysis module is disposed upstream of the sorting station.

* * * * *

UNITED STATES PATENT AND TRADEMARK OFFICE

CERTIFICATE OF CORRECTION

PATENT NO. : 7,807,454 B2
APPLICATION NO. : 11/583989
DATED : October 5, 2010
INVENTOR(S) : Sang-Hyun Oh et al.

It is certified that error appears in the above-identified patent and that said Letters Patent is hereby corrected as shown below:

Column 1, beginning at line 5, insert the following paragraph between the title and the BACKGROUND heading: --This invention was made with Government support under Grant No. N00014-04-1-0456, awarded by the Office of Naval Research. The Government has certain rights in this invention.--

Column 35, Claim 5, line 44, delete the phrase “magnetic field gradient generator comprise a”.

Signed and Sealed this
Twenty-second Day of February, 2011

David J. Kappos
*Director of the United States Patent and Trademark Office*

UNITED STATES PATENT AND TRADEMARK OFFICE

CERTIFICATE OF CORRECTION

PATENT NO. : 7,807,454 B2
APPLICATION NO. : 11/583989
DATED : October 5, 2010
INVENTOR(S) : Sang-Hyun Oh et al.

It is certified that error appears in the above-identified patent and that said Letters Patent is hereby corrected as shown below:

On the title page item [75] inventor: “Dharmakirthi Nawarathna” should be --Dharmakeerthi Nawarathna--.

Signed and Sealed this
Twenty-first Day of February, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Trp Val Met Ser Phe Gln Asp Tyr Lys Asp Leu Leu Lys Thr His
 1               5                  10                  15


<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Ser Gln Trp Val Gln Asp Tyr Lys Leu Leu Asp Pro Thr Arg Ser
 1               5                  10                  15
```

-continued

<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Glu Asp Gly Trp Gly Phe Asp Tyr Lys Thr Leu Asp Val Lys Leu
1 5 10 15

<210> SEQ ID NO 4
<211> LENGTH: 15
<212> TYPE: PRT
<213> ORGANISM: Artificial Sequence
<220> FEATURE:
<223> OTHER INFORMATION: synthetic peptide

<400> SEQUENCE: 4

Arg Gly Leu Arg Ser Met Phe Lys Ser Asp Tyr Lys Asp Tyr Asp
1 5 10 15

<210> SEQ ID NO 5
<211> LENGTH: 15
<212> TYPE: PRT
<213> ORGANISM: Artificial Sequence
<220> FEATURE:
<223> OTHER INFORMATION: synthetic peptide

<400> SEQUENCE: 5

Ser Asp Tyr Lys Arg Lys Asp Arg Trp Leu Ser His Glu Ser Arg
1 5 10 15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Ser Lys Leu Lys Asp Tyr Lys Met Glu Asp Met Arg Asp Asn Trp
1 5 10 15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Ser His Met Thr Asp Tyr Lys Cys Lys Asp Met Arg Gly Gly Ser
1 5 10 15

<210> SEQ ID NO 8
<211> LENGTH: 15
<212> TYPE: PRT
<213> ORGANISM: Artificial Sequence
<220> FEATURE:
<223> OTHER INFORMATION: synthetic peptide

<400> SEQUENCE: 8

Ala Asn Thr Thr Gly Ser Thr Asp Tyr Lys Ile His Asp Pro Ser
1 5 10 15